(12) United States Patent
Narum et al.

(10) Patent No.: US 7,303,751 B2
(45) Date of Patent: Dec. 4, 2007

(54) ANTI-PLASMODIUM COMPOSITIONS AND METHODS OF USE

(75) Inventors: David L. Narum, Gaithersburg, MD (US); Kim L. Sim, Gaithersburg, MD (US)

(73) Assignee: The Government of the United States of America, as represented by the Secretary, Department of Health and Human Services, Washington, DC (US)

( * ) Notice: Subject to any disclaimer, the term of this patent is extended or adjusted under 35 U.S.C. 154(b) by 455 days.

(21) Appl. No.: 10/630,629

(22) Filed: Jul. 29, 2003

(65) Prior Publication Data

US 2006/0153881 A1    Jul. 13, 2006

Related U.S. Application Data

(63) Continuation of application No. 09/924,154, filed on Aug. 7, 2001, now abandoned.

(60) Provisional application No. 60/223,525, filed on Aug. 7, 2000.

(51) Int. Cl.
A61K 39/00    (2006.01)

(52) U.S. Cl. .................................... 424/191.1; 530/350

(58) Field of Classification Search ..................... None
See application file for complete search history.

(56) References Cited

U.S. PATENT DOCUMENTS

| | | | |
|---|---|---|---|
| 3,817,837 | A | 6/1974 | Rubenstein et al. |
| 5,849,306 | A | 12/1998 | Sim et al. |
| 5,993,827 | A | 11/1999 | Sim et al. |
| 2005/0239730 | A1 | 10/2005 | Mayer et al. |

FOREIGN PATENT DOCUMENTS

| | | |
|---|---|---|
| WO | WO 00/52056 | 9/2000 |
| WO | WO 02/078603 A2 | 10/2002 |

OTHER PUBLICATIONS www.ddmag.com; definition of paralog.*
Database EMBL 'Online!' EBI; Mar. 15, 1999 "*Plasmodium falciparum* genome sequence" Database accession No. AL049180.
International Preliminary Examination Report from the priority PCT application No. PCT/US01/24725.
International Search Report from the priority PCT application No. PCT/US01/24725.
Kappe, S.H.I. et al. 1997 "Erythrocyte binding protein homologues of rodent malaria parasites." *Mol Biochem Parasitol* 89(1):137-148.
Mayer, D.C.G. et al. 2001 "Characterization of a *Plasmodium falciparum* erythrocyte-binding protein paralogous to EBA-175." *PNAS USA* Apr. 24; 98(9):5222-5227, Epub Apr. 17, 2001.
Peterson, D.S. et al. 1995 "Isolation of multiple sequences from the *Plasmodium falciparum* genome that encode conserved domains homologous to those in erythrocyte-binding proteins." *PNAS USA* 92(15):7100-7104.
Sim B.K.L. 1995 "EBA-175: an erythrocyte-binding ligand of *Plasmodium falciparum.*" *Parasitol Today* 11(6):213-217.
Triglia, T. et al. 2001 "An EBA175 homologue which is transcribed but not translated in erythrocytic stages of *Plasmodium falciparum.*" *Mol Biochem Parasitol* Aug; 116(1):55-63.
Adams, J. H., Hudson, D. E., Torii, M., Ward, G. E., Wellems, T. E., Aikawa, M., Miller, L. H. "The Duffy receptor family of *Plasmodium knowlesi* is located within the mocronemes of invasive malaria merozoites." Cell. 63: 141-153. (1990).
Adams, J. H., Sim, B. K. L., Dolan, S. A., Fang, X., Kaslow, D. C., Miller, L. H. "A family of erythrocyte binding proteins of malaria parasites." Proc. Natl. Acad. Sci. 89: 7085-7089 (1992).
Chitnis, C. E., Miller, L. H. Identification of the erythrocyte binding domains of *Plasmodium vivax* and *Plasmodium knowlesi* proteins involved in erythrocyte invasion. J Exp Med Aug. 1, 1994; 180(2):497-506.
Camus, D., and T. J. Hadley. A *Plasmodium falciparum* antigen that binds to host erythrocytes and merozoites. Science. 1985; 230, No. 4725:553.
Deans, J. A., and W. C. Jeans. 1987. Structural studies on a putative protective *Plasmodium knowlesi* merozoite antigen. Molecular Biochemical Parasitology. 26:155-166.
Dolan, S. A., J. L. Proctor, D. W. Alling, Y. Okubo, T. E. Wellems, and L. H. Miller. 1994. Glycophorin B as an EBA-175 independent *Plasmodium falciparum* receptor of human erythrocytes. Mol Biochem Parasitol. 64:55-63.

(Continued)

*Primary Examiner*—Patricia A. Duffy
(74) *Attorney, Agent, or Firm*—Knobbe, Martens, Olson & Bear, LLP

(57) ABSTRACT

Compositions that inhibit the binding of *Plasmodium falciparum* to erythrocytes include a family of erythrocyte binding proteins (EBPs). The EBPs are paralogues of the *P. falciparum* binding protein EBA-175. The present invention includes peptides of the paralogues that prevent the binding of *P. falciparum*. Antibodies specific for each paralogue that also prevent the binding of *P. falciparum* are also included. Methods of the invention utilize the paralogues, antibodies thereof and peptide compositions for the diagnosis, prevention, and treatment of *P. falciparum* diseases such as malaria, as well as methods for the detection of *P. falciparum* in biological samples and culture media.

8 Claims, 8 Drawing Sheets

OTHER PUBLICATIONS

Figure 1:
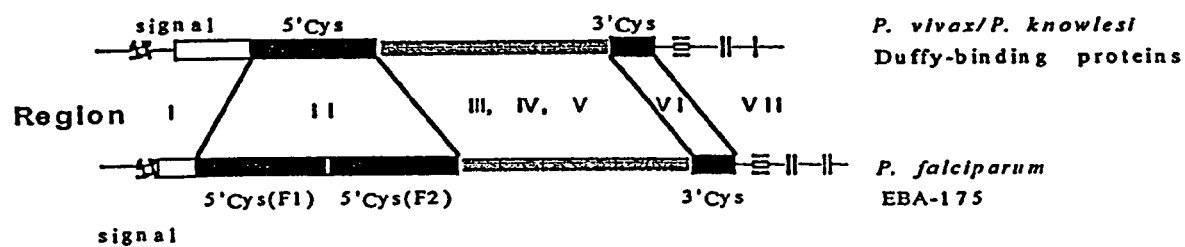
Figure 3:
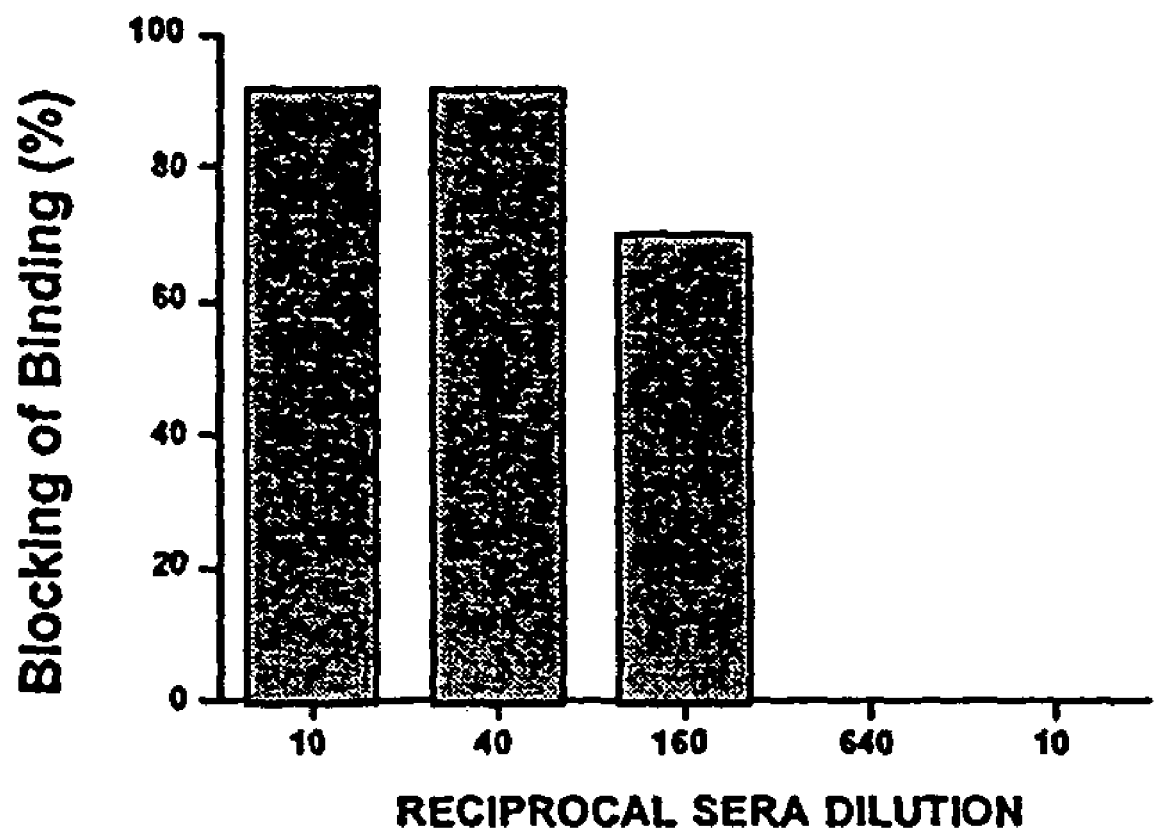

Fang, X., Kaslow, D. C., Adams, J. H., Miller, L. H. "Cloning of the *Plasmodium vivax* Duffy receptor." Mol Biochem. Parasitol. 44: 125-132 (1991).

Hadley, T. J., Erkmen, Z., Kaufman, B. M., Futrovsky, S., McGuinnis, M. H., Graves, P., Sadoff, J. C., Miller, L. H., Factors influencing invasion of erythrocytes by *Plasmodium falciparum* parasites: the effects of an N-acetyl glucosamine neoglycoprotein and an anti-glycophorin antibody. Am J Trop Med Hyg Sep. 1986; 35(5) :898-905.

Hartikka, J., Sawdey, M., Cornefert-Jensen, F., Margalith, M., Barnhart, K., Nolasco, M., Vahlsing, H. L., Meek, J., Marquet, M., Hobart, P., Norman, J., and Manthorpe, M. 1996. An improved plasmid DNA expression vector for direct injection into skeletal muscle. Hum Gene Ther. 7:1205-17.

Horuk, R., Chitnis, C. E., Darbonne, W. C., Colby, T. J., Rybicki, A., Hadley, T. J., and Miller, L. H., 1993. A receptor for the malarial parasite *Plasmodium vivax*: the erythrocyte chemokine receptor. Science. 261:1182-4.

Liang, H., Narum, D. L., Fuhrmann, S. R., Luu, T., Sim, B. K., 2000. A recombinant baculovirum-expressed *Plasmodium falciparum* receptor-binding domain of erythrocyte binding protein EBA-175 biologically mimics native protein. Infect Immun Jun; 68(6) :3564-8.

Miller, L. H., Mason, S. J., Dvorak, J. A., McGinniss, M. H., Rothman, I. K., Erythrocyte receptors for (*Plasmodium knowlesi*) malaria: Duffy blood group determinants. Science Aug. 15, 1975; 189-(4202) :561-3.

Narum, D. L., and Thomas, A. W. 1994. Differential localization of full-length and processed forms of PF83/AMA-1 an apical membrane antigen of *Plasmodium falciparum* merozoites. Mol Biochem Parasitol. 67:59-68.

Narum, D. L., Haynes, J. D., Fuhrmann, S., Moch, K., Liang, H., Hoffman, S. L., and Sim, B. K. 2000. Antibodies against the *Plasmodium falciparum* receptor binding domain of EBA-175 block invasion pathways that do not involve sialic acids [In Process Citation]. Infect Immun. 68:1964-6.

Orlandi, P. A., Sim, B. K., Chulay, J. D., and Haynes, J. D. 1990. Characterization of the 175-kilodalton erythrocyte binding antigen of *Plasmodium falciparum*. Mol Biochem Parasitol. 40:285-94.

Orlandi, P. A., Klotz, F. W., and Haynes, J. D. "A malaria invasion receptor, the 175-kilodalton erythrocyte binding antigen of *Plasmodium falciparum* recognizes the terminal neu5Ac((2-3) galsequences of glycophorin A." J. Cell Biol. 116:901-909 (1992).

Sim, B. K., Orlandi, P. A., Haynes, J. D., Klotz, F. W., Carter, J. M., Camus, D., Zegans, M. E., and Chulay, J. D. Primary structure of the 175K *Plasmodium falciparum* erythrocyte binding antigen and identification of a peptide which elicits antibodies that inhibit malaria merozoite invasion. J Cell Biol. 1990; 111, No. 5 Pt 1:1877-1884.

Sim, B. K. L., Chitnis, C. E., Wasniowska, K., Hadley, T. J., Miller, L. H., Receptor and ligand domains for invasion of erythrocytes by *Plasmodium falciparum*. Science. 264:1941-1944. (1994).

Sim, B. K. L., Toyoshima, T., Haynes, J. D., and Aikawa, M. 1992. Localization of the 175-kilodalton erythrocyte binding antigen in micronames of *Plasmodium falciparum* merozoites. Mol Biochem Parasitol. 51:157-9.

Vernes, A., Haynes, J. D., Tapchaisri, P., Williams, J. L., Dutoit, E., Diggs, C. L., *Plasmodium falciparum* strain-specific human antibody inhibits merzoite invasion of erythrocytes. Am J Trop Med Hyg Mar. 1984;33(2) :197-203.

Hadley, T.J., "Invasion of erythrocytes by malaria parasites: a cellular and molecular overview." Annu Rev. Microbiol. (1986);40:451-77.

\* cited by examiner

Fig. 2A

```
Majority   D F G G N S D X V E E X I K K X F K X - Y X - - - - - - - - - - E - N - E K - -
                     290             300             310             320
EBP1.SEQ   D P G G Y S T K A E N K I Q E V F K G A H G - - - - - - - - - E I S E H K I K    841
EBP2.SEQ   D F G G N T D R V K G Y I N K K F S D Y K - - - - - - - - - - E K N V E K L N    844
EBP3.SEQ   I Y K N N T D Y I K E Q F K K I F N N E Y N N N E L N D E L N N E L N D E K N I  538
EBP4.SEQ   - - - - - - - - - - - - - - - - - - - - - - - - - - - - - - - - - - - - - - -  100
EBP5.SEQ   D K N N I S K L V E E S L K R F F K - - D S S V L N - - - - - - - - - - - - -    754

Majority   N - R K E W W E K Y K E X L W E X M I X E H K X N I - - - C K X I P X E E P Q I
                     330             340             350             360
EBP1.SEQ   N F R K K W W N E F R E K L W E A M L S E H K N N I N N - C K N I P Q E E L Q I  958
EBP2.SEQ   N I K E W W E K N K A N L W N H M I V N H K G N I S K E C A I I P A E E P Q I    964
EBP3.SEQ   K L R K E W W E K Y K E D I W E E M T K E H N D K F I E K C K Y F A K D E P Q I  658
EBP4.SEQ   - - - - - - - - - - - - - - - - - - - - - - - - - - - - - - - - - - - - - - -  100
EBP5.SEQ   - - P T A W W R R Y G T R L W K T M I Q P Y A H L - - - G C R K P D E N E P Q I  859

Majority   N R W I K E W X K - - - X F L X E K X X L L - - - K X K C X E N X K Y E A C - -
                     370             380             390             400
EBP1.SEQ   T Q W I K E W H G - - - E F L E R D N R S K L P K S K C K N N T L Y E A C E K    1069
EBP2.SEQ   N L W I K E W N E - - - N F L M E K R L F L N I K D K C V E N K K Y E A C F G    1075
EBP3.SEQ   V R W I E W S K - - - Q F L D E K N Y M L F T L R N T Y N E M N I I H E - - -    760
EBP4.SEQ   - - - - - - - - - - - - - - - - - - - - - - - - - - - - - - - - - - - - - - -  100
EBP5.SEQ   N R W I L E W G K Y N C R L M K E K E K L L - - - T G E C S V N R K S D C S T    970

Majority   G C X N E C K K Y R S W I X K S K X E W T I L S N E Y - - - - - - - - - N K K X
                     410             420             430             440
EBP1.SEQ   E C I D P C M K Y R D W I R S K F E W H T L S K E Y - - - - - - - - E T Q K      1162
EBP2.SEQ   G C R L P C S S Y T S F M K K S K T Q M E V L T N L Y - - - - - - - - K K K N    1168
EBP3.SEQ   - - - N N C K Q Y N K W V Q N R K E W T F L S N E F - - - - - - - - N K I -      841
EBP4.SEQ   - C K S E C K K Y K A W I D K K N N D F T I L S E I Y L K - - - - - - Y N K K S  199
EBP5.SEQ   G C N N E C Y T Y R S L I N R Q R Y E V S I L G K K Y I K V V R Y T I P R R K I  1090

Majority   V P X D N A X N F L K X I F K E Y K D N D V S X I F X N L N A E Y X N K C D C Q
                     450             460             470             480
EBP1.SEQ   V P K E N A E N Y L I K I S E N K N D A K V S L L L N C D A E Y S K Y C D C K    1282
EBP2.SEQ   S G V D K - N N F L N D L F K N N K N D L D D F F K N - E K E Y D D L C D C R    1282
EBP3.SEQ   F P E R N V Q I H I S N I F K E Y K E N N V D I I P G T L N Y E Y N N F C K E K  961
EBP4.SEQ   S L Y K T A F E Y L K Q K W D K Y K E L N F S S L I P D Q L N A K Y Y N K C I C Q  319
EBP5.SEQ   V Q P D N A L D F L K L N C S E C K D I D F K P F F E F E Y G K Y R E K C M C Q  1210

Majority   X T - I T L X K S F L K G N D I C S X N I X X X I X X X D L S - F G C K E K S -
                     490             500             510             520
EBP1.SEQ   H T - T T L V K S V L N G N D N T I K E K R E H I D L D D F S K F G C D K N S V  1399
EBP2.SEQ   Y T - A T I I K S F L N G P A K N D V D I A S Q I N V N D L R G F G C N Y K S -  1396
EBP3.SEQ   P E L V S A A K Y N L K A P N A K S P R I Y K S K E H E E S S V F G C K T K - I  1078
EBP4.SEQ   N N K I E N N A L Y V K I E D I C N - N T K V K S I Y G E L - - Y - C K E K G -  424
EBP5.SEQ   S Y - I D L K I Q F - K N N D I C S F N A Q T D T V S S D K R - F - C L E K K -  1315

Majority   - - N K X X W N C - K X X F K X X X P - G V C G P P R R Q Q L C L G N L - Y L L
                     530             540             550             560
EBP1.SEQ   D T N T K V W E C - K K P Y K L S T K - D V C V P P R R Q E L C L G N I - D R I  1510
EBP2.SEQ   - N N E K S W N C - T G T F T N K F P - G T C E P P R R Q T L C L G R T - Y L L  1504
EBP3.SEQ   S K V K K W N C - Y S N N K V T K P E G V C G P P R R Q Q L C L G Y I - F L I    1192
EBP4.SEQ   - - N D K I W Q C I N E H I K D F P D - - V C G P P R R Q Q L C L G N L D - - -  523
EBP5.SEQ   - - E F K P W K C D K N S F E T V H H K G V C V S P R R Q G F C L G N L N Y L L  1429
```

Fig. 2B

```
Majority    X D G - - - - - N L E X L K E H I L X A A I Y E G K L L K E K Y K N K - - - - -
                       570              580              590              600
EBP1.SEQ    Y D K - - - - - N L M I K E H I L A I A I Y E S R I L K R K Y K N K - - - - -  1600
EBP2.SEQ    H R G - - - - - H E E D Y K E H L L G A S I Y E A Q L L K Y K Y K E K - - - - -  1594
EBP3.SEQ    R D G - - - - - N E E G L K D H I N K A A N Y E A M H L K E K Y E N A - - - - -  1282
EBP4.SEQ    K D E F K N V N D L K K F L N E I I L G I R D E G K F L I E K Y R K N M H E N M   643
EBP5.SEQ    N D D I Y N V H N - S Q L L I E I I M A S K Q E G K L L W K K - - - - - H G T I  1531

Majority    - D D X X A C K I I N X S Y A D I K D I I X G X D X W N D X N S I K L E N L N
                       610              620              630              640
EBP1.SEQ    - D D K E V C K I I N K T F A D I R D I I G G T D Y W N D L S N R K L V G K I N  1717
EBP2.SEQ    - D E N A L C S I I Q N S Y A D L A D I I K G S D I I K D Y Y G K K M E N L N    1711
EBP3.SEQ    - G G D K I C N A I L G S Y A D I G D I V R G L D V W R D I N T N K L S E K F Q  1399
EBP4.SEQ    Y L D E R A C K Y L N Y S F D D Y K N I I L G K D M W R D P N S I K T E N I L K   763
EBP5.SEQ    L D N Q N A C K Y I N D S Y V D Y K D I V I G N D L W N D N N S I K V Q N N L N  1651

Majority    K I F E X N X G X R N K Q - - - - - - - - - - S L K E F R N K W W D X N K N X V
                       650              660              670              680
EBP1.SEQ    T N - - S N Y V H R N K Q - - - - - - - - - - N D K L F R D E W K V I K D V    1801
EBP2.SEQ    K V - - N K D K K R N E E - - - - - - - - - - S L K I F R E K W W D E N K E N V  1795
EBP3.SEQ    K I F M G G G N S R K K Q - - - - - - - - - - N D N N E R N K W W E K Q R N L I  1489
EBP4.SEQ    G N F E - - - G I K A N I V S M Y P S Y A D L S L D E F R K H W W D Q N K K Q L   874
EBP5.SEQ    L I F E R N F G Y K V G R N K L F K T - - - - - I K E L K N V W W I L N R N K V  1756

Majority    W E V M S C V I - - - - K X K K T C K R X D D F E N I P Q F L R W F S E W G D D
                       690              700              710              720
EBP1.SEQ    W N V I S W V F - - - - K D K T V C K E - D D I E N I P Q F F R W F S E W G D D  1906
EBP2.SEQ    W K V M S A V L - - - - K N K E T C K D Y D K F Q K I P Q F L R W F K E W G D D  1903
EBP3.SEQ    W S S M V K H I - - - - P K G K T C K R H N N F E K I P Q F L R W L K E W G D E  1597
EBP4.SEQ    W E A I S C E F Y K G N H T - G V C L M E D D N D N - - Q Y L H W F R E W K N D   985
EBP5.SEQ    W E S M R C G I D E V D Q R R K T C E R I D E L E N M P Q F F R W F S Q W A H F  1876

Majority    F C E D K X - - - - - - K E I C X X E K X K V E C K X K N C S D - - X X C K N K
                       730              740              750              760
EBP1.SEQ    Y C Q D K T - - - - - - K M I - - - E T L K V E C K E K P C E D - - D N C K R K  1993
EBP2.SEQ    F C E K R K - - - - - - E K I Y S F E S F K V E C K K K D C D E - - N T C K N K  1999
EBP3.SEQ    F C E E M G - - - - - - T E V K Q L E K I - - - C E N K N C S E - - K K C K N A  1684
EBP4.SEQ    F C I D K L K W N D V I K E P C I D K L V K S P K P S E N P S D V A T V C N K S  1105
EBP5.SEQ    F C K E K E Y W E L K L N D K C T G N N G K S L C Q D K T - - - - - - - C Q N V  1975

Majority    C S S Y K K W I X X K K K E Y E K Q S K K Y D K D K K L F N N Y - - Y - E F K D
                       770              780              790              800
EBP1.SEQ    C N S Y K E W I S K K E Y N K Q A K Q Y E Y Q K - G N N Y K M Y S E F K S       2110
EBP2.SEQ    C S E Y K K W I D L K K S E Y E K Q V D K Y T K D K N - K K M Y D N I D E V K N  2116
EBP3.SEQ    C S S Y E K W I K E R K N E Y N L Q S K K F D S D K K L N K K N N L Y N K F E D  1804
EBP4.SEQ    C T D Y D K W I I N K R K E Y K M Q S S K Y K R D R S L F N N V - - - - - I Q N  1210
EBP5.SEQ    C T N M N Y W T Y T R K L A Y E I Q S V K Y D K D R K L F S - L - - - - - A K D  2077

Majority    K K A X V Y L K E X S K K C S N I N F X D E I F X E L P N X Y K E X C T - C X -
                       810              820              830              840
EBP1.SEQ    I K P E V Y L K Y S E K C S N L N F E D F K E L H S D Y K N K C T M C P -       2227
EBP2.SEQ    K E A N V Y L K E K S K E C K D V N F D D K I F N E S P N E Y E D M C K K C D -  2233
EBP3.SEQ    S K A - - Y L R S E S K Q C S N I E F N D E T F T - F P N K Y E A C M V C E -    1912
EBP4.SEQ    L K P W E Y L - - - S M K C T E - - - - - - - - - - - - - - C T - C N L          1264
EBP5.SEQ    K N V T T F L K E N A K N C S N I D F T - K I F D Q L D K L F K E R C S - C - M  2188
```

ANTI-PLASMODIUM COMPOSITIONS AND METHODS OF USE

CROSS REFERENCE TO RELATED APPLICATIONS

This application is a continuation and claims the benefit of priority of U.S. patent application Ser. No. 09/924,154 filed Aug. 7, 2001, now abandoned which claims the benefit of priority of U.S. Provisional Appl. No. 60/223,525 filed Aug. 7, 2000, both of which are hereby expressly incorporated by reference in their entireties.

FIELD OF THE INVENTION

The present invention relates to the fields of microbiology and immunology and more specifically relates to compositions and methods for the detection, diagnosis, prevention and treatment of malaria. In particular, the invention pertains to a family of paralogues of EBA-175, antibodies specific to each paralogue, peptides of the paralogues and peptides of the antibodies that inhibit the binding of Plasmodium falciparum erythrocyte binding protein antigens to erythrocytes.

BACKGROUND OF THE INVENTION

Although endemic malaria has disappeared from the United States, malaria continues to be one of the most important infectious diseases in the world as it kills millions of people each year in countries throughout Africa, Asia and Latin America. The characteristic presentation of malaria is chills followed by a fever ranging from 104-107° F., followed by profuse sweating. Other manifestations of malaria include anemia, decreased blood flow to vital organs, thrombocytopenia, and glomerulonephritis. Additionally, when the central nervous system is involved, symptoms include delirium, convulsions, paralysis, coma, and even rapid death.

Malarial diseases in humans are caused by four species of the Plasmodium parasite: Plasmodium falciparum (Pf), Plasmodium vivax (Pm), Plasmodium ovali (Po), and Plasmodium malariae (Pm). Each of these species is transmitted to the human via a female Anopheles mosquito that transmits Plasmodium parasites, or sporozoites. Once the sporozoites enter the bloodstream of the human, they localize in liver cells, or hepatocytes. One to two weeks later, the infected hepatocytes rupture and release mature parasites, or merozoites. The merozoites then begin the erythrocytic phase of malaria by attaching to and invading red blood cells, or erythrocytes.

The invasion of the erythrocytes by the malarial parasites is the direct cause of malarial pathogenesis and pathology. The fever, anemia, circulatory changes, and immunopathologic phenomena characteristic of malaria are largely the result of red cell rupture and the host's immune response to parasitized erythrocytes. For these reasons, the erythrocytic stage of the Plasmodium life cycle is of vital importance to vaccine development and treatment of malaria.

There are a number of strategies for developing new or novel therapeutics for the erythrocytic stage of malaria. One strategy is to identify parasitic molecules that are critical to the survival of the parasite. Extracellular merozoites released from infected hepatocytes or from infected erythrocytes must invade other erythrocytes within minutes if they are to survive. Invasion by the malaria parasite is dependent upon the binding of parasite proteins to receptors on the erythrocyte surface (Hadley et al., 1986).

Interestingly, different parasite species use different erythrocytic receptors for invasion of erythrocytes. P. falciparum invades erythrocytes through a 175 kDa erythrocyte binding protein called EBA-175. The gene encoding EBA-175 of Pf has been cloned and sequenced (Sim et al., 1990; Fang et al., 1991). EBA-175 functions as an erythrocyte invasion ligand that binds to its receptor, glycophorin A, on erythrocytes during invasion (Camus and Hadley, 1985; Sim et al., 1990; Orlandi et al., 1992; Sim et al., 1994b). In contrast, the human P. vivax and the simian P. knowlesi invade erythrocytes by binding Duffy blood group antigens present on some erythrocytes (Miller et al., 1975). The genes encoding the Duffy antigen binding proteins of P. vivax and P. knowlesi have been cloned and sequenced (Fang et al., 1991 and Adams et al., 1990, respectively).

Sequencing of the genes encoding the proteins used by P. vivax and P. knowlesi for erythrocyte invasion demonstrated that these proteins are members of the same gene family as the genes that encode the EBA-175, the protein used by P. falciparum for erythrocyte invasion (Adams et al., 1992). Homology between the Duffy binding proteins and EBA-175 is restricted to 5' and 3' cysteine rich domains. Within these cysteine rich domains, the cysteines and some aromatic residues are conserved, but the intervening amino acid sequences differ. Sim et al. (1994b) demonstrated that the 5' cysteine rich domain of EBA-175 of P. falciparum contains the receptor binding domain, while Chitnis and Miller (1994) demonstrated that the 5' cysteine rich region of P. vivax and P. knowlesi contain the Duffy binding domain. See FIG. 1.

What is needed for erythrocytic malaria vaccine development is the identification and targeting of parasite molecules involved in the process of erythrocyte invasion. Blockade of this ligand-receptor-mediated event can inhibit parasite development in vitro.

Invasion of erythrocytes by malaria parasites results from merozoite ligands interacting with erythrocyte receptors. Within Plasmodium a family of merozoite ligands (orthologues) that are erythrocyte-binding proteins (EBPs) has been identified. In the most severe human malaria, Plasmodium falciparum, the EBP is identified as the erythrocyte binding protein-175 (or EBA-175), and in P. vivax, the second most prevalent human malaria and the simian malaria P. knowlesi, the EBPs are termed the Duffy antigen binding proteins (PvDABP or PkDABP, respectively). Analysis of the deduced amino sequence of these orthologous proteins (EBA-175, PvDABP and PkDABP) lead to the classification of seven distinct domains encoding regions of greater or lesser similarity (Adams et al. 1992). Within the molecular family, two regions show significant levels of conservation, these are identified as region II (RII), which encodes for the ligand-binding domain and region VI (RVI), which has as yet an unknown function. EBA-175 RII binds sialic acid residues in conjunction with the peptide backbone of glycophorin A. PvDABP and PkDABP RII bind the Duffy blood group antigens, which are chemokine receptors (Horuk et al. 1993). PvDABP and PkDABP have a single cysteine rich domain (termed F1) while EBA-175 RII contains essentially a duplicate of F1, termed F1 and F2. Both RII and RVI domains contain cysteine rich motifs. One function of RII and RVI is apparently to provide for a conserved tertiary structure, critical for the ligand-receptor interaction that leads to erythrocyte invasion. Erythrocytic invasion by P. vivax merozoites appears dependent on the Duffy blood group antigens while in vitro studies have shown that P. falciparum may use alternative invasive pathways (Narum et al. 2000, Dolan et al. 1994).

SUMMARY OF THE INVENTION

The present invention provides compositions and methods for detecting, diagnosing, preventing and treating Plasmodium falciparum and Plasmodium falciparum related infections. In particular, the compositions include a family of merozoite ligands that are erythrocyte binding proteins (EBPs). The EBPs of the invention are paralogues of EBA-175, an EBP in *P. falciparum*. The invention further comprises antibodies specific to each paralogue, peptides of the paralogues, and peptides of the antibodies that specifically inhibit binding of *P. falciparum* erythrocyte binding proteins to erythrocytes.

The cysteine residues of the EBPs are conserved within the erythrocyte binding domain of EBA-175 RII. Some of the family members of the present invention include EBP2 (SEQ ID NO:1), EBP3 (SEQ ID NO:2), EBP4 (SEQ ID NO:3), and EBP5 (SEQ ID NO:4).

More specifically, the paralogues and respective peptides of the invention are useful as potential vaccine candidates, targets for producing antibodies, targets for small blocking peptides, and diagnostics.

The compositions also include *P. falciparum* antibodies to the family of EBA-175 paralogues and antibody fragments thereto, *P. falciparum* blocking peptides derived from the paralogues and/or antibodies thereto, *P. falciparum* antisera, *P. falciparum* receptor agonists and *P. falciparum* receptor antagonists linked to cytotoxic agents. Such compositions are also useful for research applications, as vaccine candidates, as blocking peptides, diagnostics and prognostics. The compositions, when combined with pharmaceutically acceptable excipients, or sustained-release compounds or compositions, such as biodegradable polymers, are useful as therapeutic agents such as vaccine or treatment compositions.

Diagnostic and analytical methods and kits may be developed for detection and measurement of *P. falciparum* in a variety of biological samples including biological fluids and biological tissues, and for localization of *P. falciparum* in tissues and cells. The method and kit can be in any configuration well known to those of ordinary skill in the art.

The methods of the present invention include methods of treating, diagnosing and preventing *P. falciparum* diseases such as malaria. These methods employ the family of paralogues of the EBA-175 protein, the antibodies specific for individual paralogues and the blocking peptides described herein. Methods of prevention may include passive immunization prior to infection by *Plasmodium falciparum* parasites to inhibit parasitic infection of erythrocytes. Methods of treatment may also include administration after infection to inhibit the spread of the parasite and ameliorate the symptoms of *P. falciparum* infection. Methods of diagnosis of *P. falciparum* infection include methods directed toward combining a biological sample with the paralogues and/or antibodies described herein, wherein the binding of the paralogues and/or antibodies indicates malaria. Methods of detection of *P. falciparum* and *P. falciparum* erythrocyte binding proteins include methods directed toward the detection of *P. falciparum* and *P. falciparum* erythrocyte binding proteins or antibodies thereto in biological samples such as biological fluids, tissues and in culture media.

Also provided are methods of detecting additional family members of the paralogues of *P. falciparum* and *P. falciparum* erythrocyte binding proteins. Criteria include the identification of regions within malaria proteins that likely share a molecular structure that function as a receptor binding domain as identified by homology between EBP region II (F1 and/or F2) and/or region VI. The ligand binding region of interest is primarily the disulfide forming amino acid cysteine rich region which also includes other aromatic amino acids such as proline and tryptophan.

Accordingly, it is an object of the present invention to provide compositions comprising one or more paralogues of *P. falciparum* erythrocyte binding protein, antibodies specific for each paralogue or blocking peptides derived from the paralogues or antibodies.

It is another object of the present invention to provide a method for the treatment of *P. falciparum* related diseases such as malaria.

It is a further object of the present invention to provide a method for the treatment of malaria, wherein compositions comprising one or more paralogues of *P. falciparum* erythrocyte binding protein, antibodies specific for each paralogue and/or blocking peptides derived from the paralogues or antibodies are administered to an individual in need of such treatment.

It is another object of the present invention to provide a method for the diagnosis of *P. falciparum* related diseases such as malaria.

It is yet another object of the present invention to provide a method for the diagnosis of malaria, wherein compositions comprising one or more paralogues of *P. falciparum* erythrocyte binding protein, and/or antibodies specific for each paralogue are used.

A further object of the present invention is to provide a method for the prevention of *P. falciparum* related diseases such as malaria.

It is another object of the present invention to provide a method for the prevention of malaria, wherein compositions comprising one or more paralogues or regions thereof of *P. falciparum* erythrocyte binding protein, antibodies specific for each paralogue and/or blocking peptides derived from the paralogues or antibodies are administered to an individual in need of such prevention.

Another object of the present invention to provide a method of detection of *P. falciparum* in culture media and in biological samples such as biological tissues and fluids.

It is a further object of the present invention to provide a method of detection of *P. falciparum*, wherein compositions comprising one or more paralogues of *P. falciparum* erythrocyte binding protein and/or antibodies specific for each paralogue are used.

These and other objects, features and advantages of the present invention will become apparent after a review of the following detailed description of the disclosed embodiments and the appended claims.

BRIEF DESCRIPTION OF THE FIGURES

FIG. 1: Gene Structure of *Plasmodium* Erythrocyte Binding Proteins

Region I of EBA-175 encompasses amino acid residues 20-157, region II amino acids 145-760, region III-V amino acids 743-1322 and region VI amino acids 1304-1394. Region II is further subdivided into regions F1 and F2.

Figure 2A:
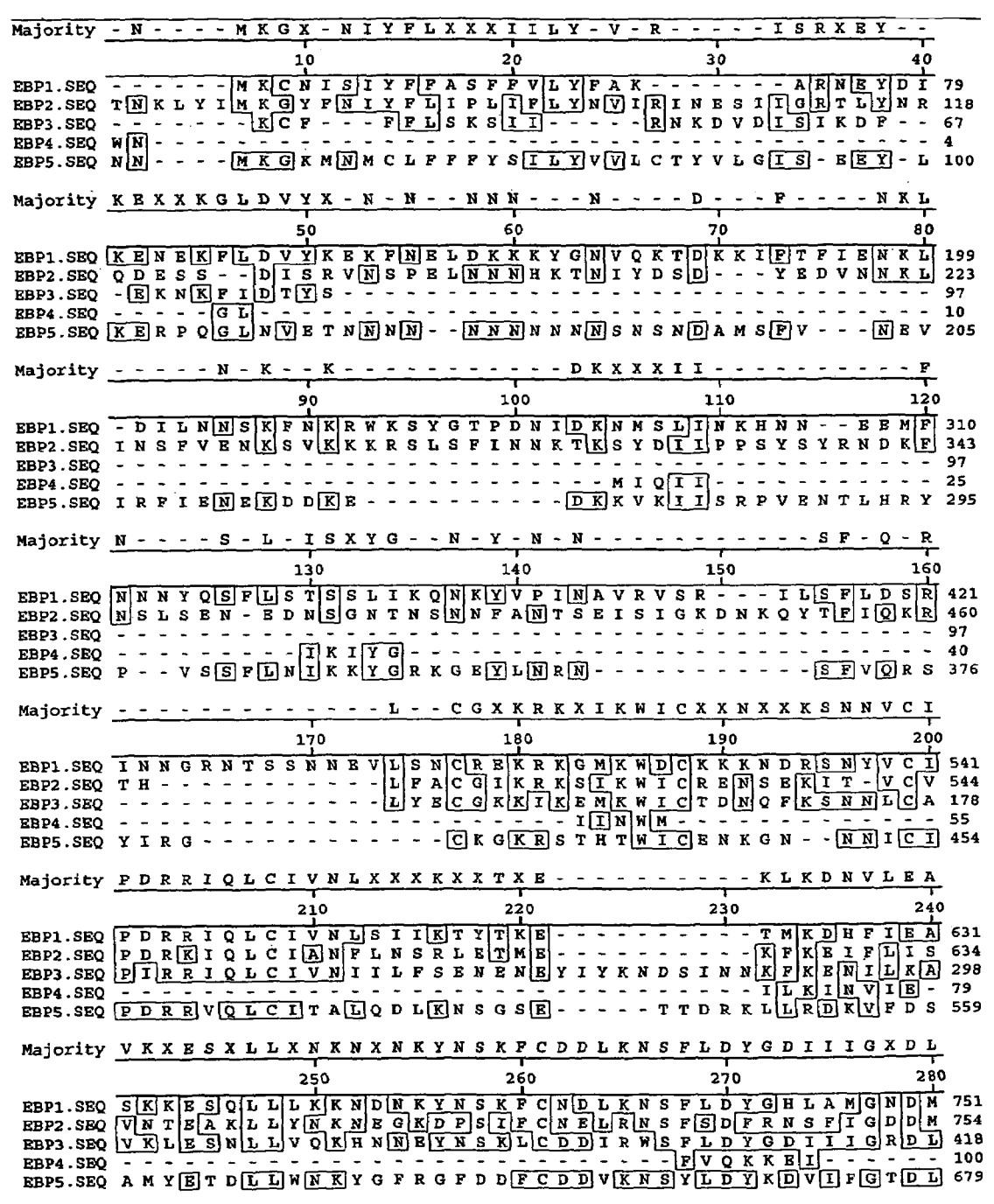
Figure 2D:
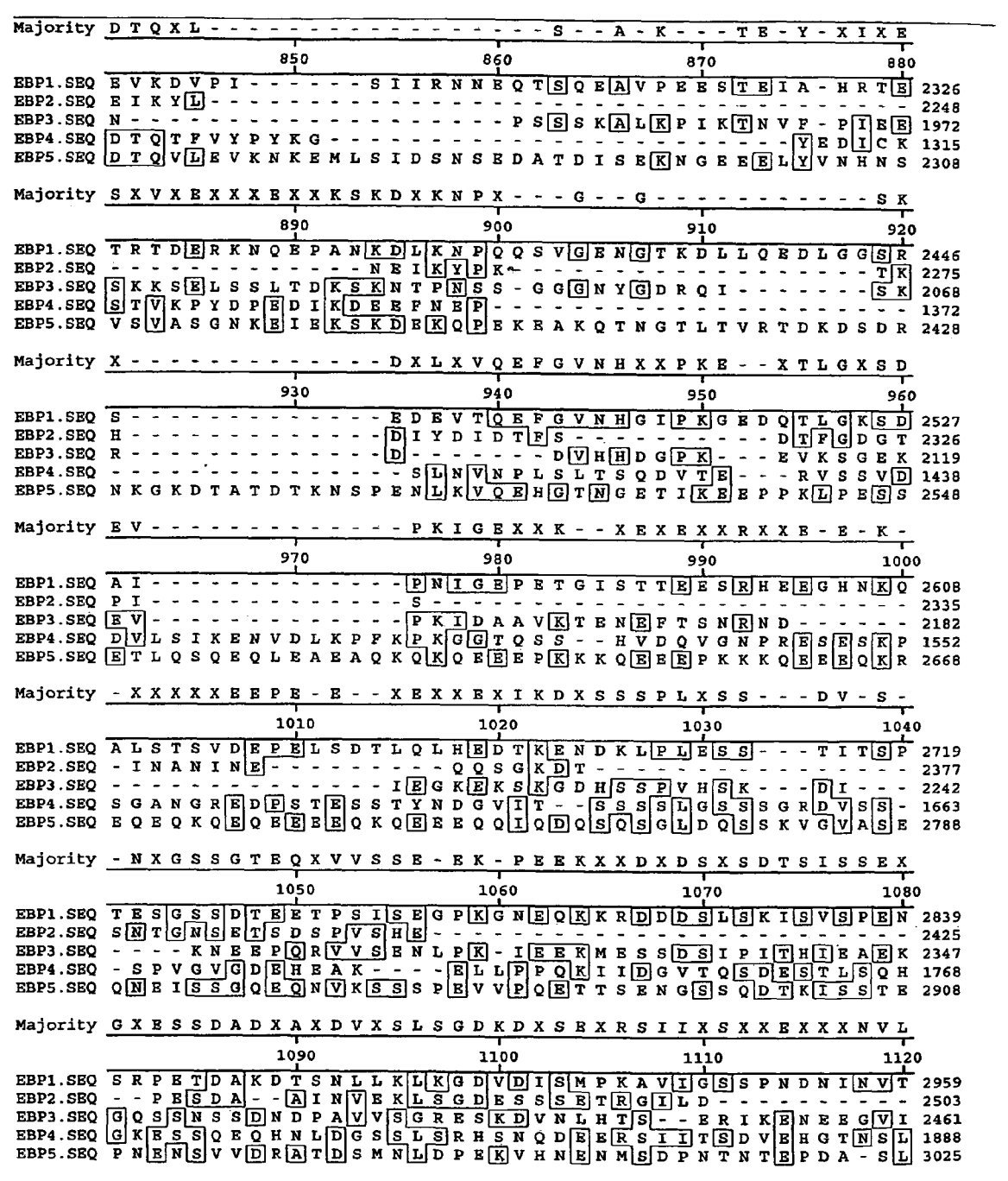
Figure 2E:
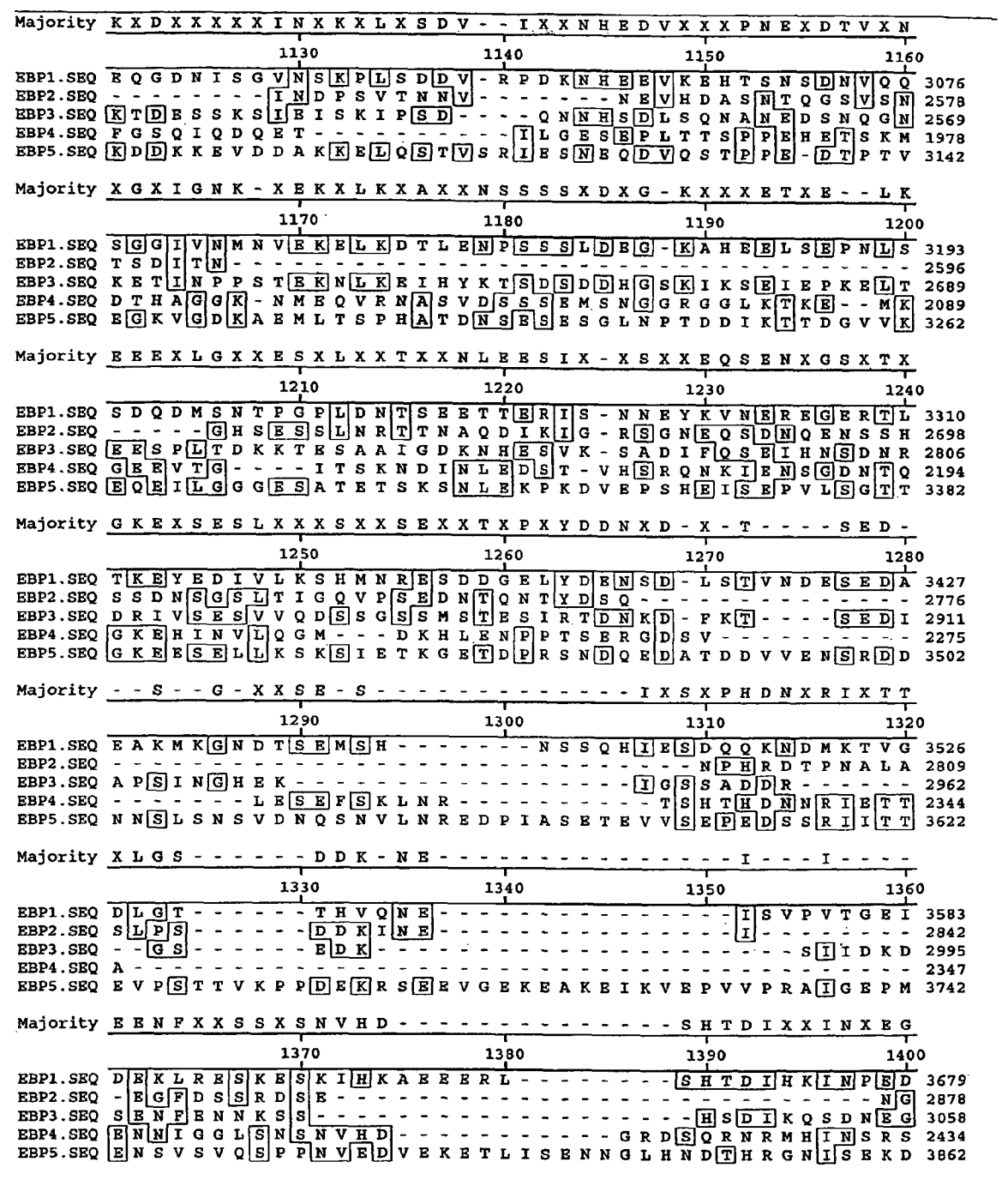
Figure 2F:
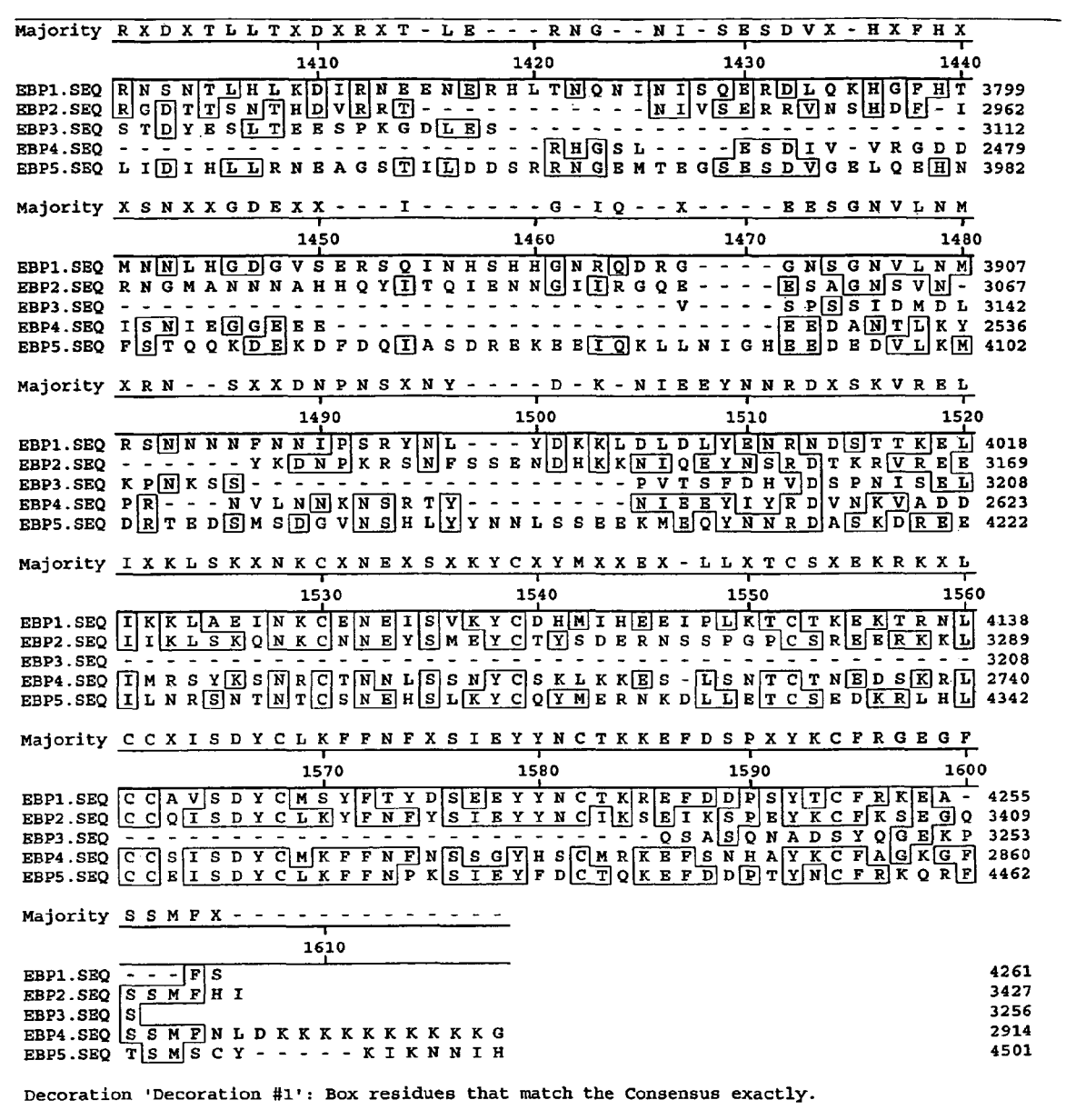

FIG. 2: Nucleotide and deduced amino acid sequence alignment of five EBA-175 Blocking Peptides Nucleotide and deduced amino acid sequence alignment of partial ORF of eba-175 (ebp1) (SEQ ID NO: 18), ebp2 (SEQ ID NO: 1), ebp3 (SEQ ID NO: 2), ebp4 (SEQ ID NO: 3) and ebp5 (SEQ ID NO: 4). Identical amino acid residues are shown in boxes.

FIG. 3: EBP2 specific polyclonal antibodies blocked EBP2 binding to human erythrocytes The blocking of binding of processed fragments of EBP2 with erythrocytes as a percent compared to the control which was determined at a 1/10 dilution. Equal volumes of erythrocyte lysate were immunoprecipitated with EBP2 specific polyclonal antibodies.

DETAILED DESCRIPTION

Compositions and methods for preventing and treating *P. falciparum* infection, diagnosing diseases related to *P. falciparum* infection, and preventing diseases related to *P. falciparum* infection are provided. The compositions include at least one of a family of paralogues, antibodies specific for each paralogue and peptides derived from the paralogues and antibodies that specifically inhibit binding of *P. falciparum* erythrocyte binding proteins and fragments thereof. The paralogues, antibodies and fragments thereof are useful in malaria vaccines and for receptor blocking therapies.

More specifically, a family of paralogues to the EBA-175 erythrocyte binding protein (EBP) has been identified in *P. falciparum*. The cysteine residues of the EBPs are conserved within the erythrocyte binding domain of EBA-175 RII. The RII region was previously disclosed in U.S. Provisional Patent Application Nos. 60/122,842, 60/153,575, PCT/US00/05820, and U.S. Pat. Nos. 5,993,827 and 5,849,306 to Sim et al., each of which is herein incorporated by reference. Examples of the family members of the present invention are shown in FIG. 2 and include EBP2 (SEQ ID NO:1), EBP3 (SEQ ID NO:2), EBP4 (SEQ ID NO:3), and EBP5 (SEQ ID NO:4). FIG. 2 is an alignment report of EBP1_5 070500. MEG, using Clustal method with PAM250 residue weight table.

Characteristics of the family members include conservation of the cysteine rich domains identified as RII (F1 and/or F2), and/or RVI described herein. Members of this family are chosen by the identification of either of these regions independently or as a protein that contains both regions. Molecules with only a RII binding domain may act as an EBP and be subject to antibody mediated blockade by a vaccine or blocking therapy formulation.

Also included in the present invention are nucleotide sequences that encode each of the paralogs of *P. falciparum* erythrocyte binding protein described herein. The compositions further include vectors containing a DNA sequence encoding at least one of the paralogues of *P. falciparum*, fragments thereof, or blocking peptides, wherein the vectors are capable of expressing *P. falciparum* paralogues, fragments thereof, or blocking peptides when present in a cell. Cells containing the vectors are also included as compositions, wherein the vectors contain a DNA sequence encoding at least one of the paralogues of *P. falciparum*, fragments thereof, or blocking peptides, and wherein the vectors are capable of expressing at least one of the paralogues of *P. falciparum*, fragments thereof, or blocking peptides, when present in the cell.

The family of paralogues of the *P. falciparum* erythrocyte binding protein (EBP) and the blocking peptides described herein are useful in vitro as research tools for studying *P. falciparum* in general and *P. falciparum* related diseases such as malaria. The family of paralogues of *P. falciparum* EBA-175 are also useful as diagnostic reagents in the immunoassays described herein.

Additionally, the paralogues of EBA-175 and blocking peptides of the present invention are useful for the production of vaccines and therapeutic compositions. Pharmaceutical compositions containing a member of the paralogue family and/or peptides such as vaccines and therapeutic formulations are provided. The methods described herein are methods for detection, diagnosis, prevention and treatment of *P. falciparum* mediated malarial infections. Assays for the detection or quantitation of *P. falciparum* antigens may employ antigens derived from a biological sample such as a biological fluid or tissue or from culture media.

Additionally, antibodies specific for each of the paralogues are provided for in this invention. The compositions and uses disclosed above for the paralogues may include the antibodies and fragments thereof in place of, or in addition to, the paralogues.

The terms "a", "an" and "the" as used herein are defined to mean "one or more" and include the plural unless the context is inappropriate.

The terms "polypeptide", "peptide", and "protein", as used herein, are interchangeable and are defined to mean a biomolecule composed of two or more amino acids linked by a peptide bond.

The term "antigen" refers to an entity or fragment thereof which can induce an immune response in a mammal. The term includes immunogens and regions responsible for antigenicity or antigenic determinants. "Antigenic determinant" refers to a region of a *P. falciparum* protein recognized by an antibody.

As used herein, the terms "detecting" or "detection" refer to quantitatively or quantitatively determining the presence of the biomolecule under investigation.

By "isolated" is meant a biological molecule free from at least some of the components with which it naturally occurs.

The terms "antibody" and "antibodies" as used herein include monoclonal antibodies, polyclonal, chimeric, single chain, bispecific, simianized, and humanized antibodies, Fab fragments, including the products of an Fab immunoglobulin expression library, and peptide antibody fragments.

The phrases "specific for", "specifically binds to", "specifically hybridizes to" and "specifically immunoreactive with", when referring to an antibody or blocking peptide, refer to a binding reaction which is determinative of the presence of a peptide or antibody in the presence of a heterogeneous population of proteins and other biologics. Thus, under designated immunoassay conditions, the specified antibodies and blocking peptides bind preferentially to a particular peptide or antibody and do not bind in a significant amount to other proteins present in the sample. Specific binding to a peptide or antibody under such conditions requires an antibody or blocking peptide that is selected for its specificity for a particular protein. A variety of immunoassay formats may be used to select antibodies and peptides specifically immunoreactive with a particular protein. For example, solid-phase ELISA immunoassays are routinely used to select monoclonal antibodies specifically immunoreactive with a protein. See, Harlow and Lane (1988) *Antibodies, A Laboratory Manual*, Cold Spring Harbor Publications, New York, for a description of immunoassay formats and conditions that can be used to determine specific immunoreactivity.

As used herein, the term "paralogue" includes different genes in the same species which are so similar in nucleotide sequence or amino acid sequence or functional regions contained within conserved regions of each molecule that they are assumed to have originated from a single ancestral gene.

As used herein, the term "vaccine" includes compositions comprising the paralogues of the invention, blocking or neutralizing antibodies, or fragments thereof, or blocking peptides or fragments of the paralogues, used for passive immunization of individuals prior to or following infection by *P. falciparum*. Vaccines are known in the art and are used to stimulate immune response in the body by creating antibodies or activated T lymphocytes capable of controlling the infecting organism. The result is protection against a disease with the duration of the protection depending on the particular vaccine. The immune system produces antibodies and memory cells for pathogens so that subsequent exposure does not result in disease. A successful vaccine does the same thing, usually without risk of illness.

Vaccines can comprise four general classes: those containing infectious agents killed by physical or chemical means; those containing living attenuated infectious organisms; those containing soluble toxins or microorganisms; and those containing substances extracted from the infectious agents. Means of administering vaccines include, but are not limited to, orally or parenterally by injection, preferably by subcutaneous or intramuscular injection. Preparation and administration of oral vaccines are disclosed in U.S. Pat. No. 6,103,243, incorporated herein by reference.

The terms "blocking antibodies" or "neutralizing antibodies" refer to antibodies that bind specifically to P. falciparum antigens. The term "blocking peptides" refers to peptides that specifically inhibit the binding of P. falciparum to an erythrocyte. More particularly, the term "blocking peptides" refers to peptides that specifically inhibit the binding of an EBA-175 erythrocyte binding protein to an erythrocyte.

The compositions of the present invention include at least one member of a family of paralogues to P. falciparum erythrocytic binding protein EBA-175. P. falciparum erythrocytic binding proteins are P. falciparum derived proteins that bind to residues or proteins present on erythrocytes and facilitate P. falciparum invasion of erythrocytes.

The compositions of the present invention also include portions of the paralogues for use as blocking peptides that specifically inhibit binding of P. falciparum erythrocytic binding proteins to erythrocytes. In another preferred embodiment, the blocking peptides have a length within the range of 5-15 amino acids. Preferably, the length is within the range of 9-11 amino acids. In an alternate embodiment, there is a cysteine residue cap on each end of the blocking peptide. When creating the blocking peptides of the present invention, it is to be noted that the peptides may optionally comprise a carboxy-terminal amino acid sequence of GGGS (SEQ ID NO:5) as is well known in phage display techniques.

A preferred embodiment of the invention is the EBP2 paralogue of P. falciparum EBA-175. The EBP2 paralogue has a partial open reading frame (ORF) of a gene that shared the conserved cysteine rich motif of the EBP family and especially of EBA-175 RII (F1 and F2) although the overall amino acid identity was less than 25% (shown in FIG. 2).

The ORF of the EPB2 gene sequence was compared to the P. falciparum 3D7 strain EBA-175 region I to VI. The overall level of amino acid identity was 24.7% by the Lipman-Pearson Method of analysis. A comparison of EBA-175 region II, identified as the ligand-receptor binding domain for its receptor glycophorin A, demonstrated almost complete conservation of the cysteine residues (26 out of 27). Comparison of RII alone by the Lipman-Pearson Method of analysis showed 37.9% level of conservation when identical amino acids and conserved substitutions were included. EBA-175 RII contains two domains that have similar cysteine motifs (F1 and F2). EBP2 has a similar structural arrangement, identified here as F1 and F2. The unique deletion of a cysteine residue was found in F1 (FIG. 2). Other structural amino acids, proline (6 out of 12) and tryptophan (13 out of 13) were also conserved. Another conserved region identified earlier within EBA-175 and DABP (Adams et al., 1992 PNAS), with an unknown function, is RVI. Comparison of the EBP2 RVI and EBA-175 RVI deduced amino sequence showed that the cysteine residues were completely conserved (8 out of 8). The level of amino acid conservation (identity and conserved substitutions) was 41.6% by the same analysis as described above.

The gene ebp2 is apparently located on chromosome 13. The ORF of the ebp2 gene encodes for two regions that are conserved between P. falciparum, P. vivax and P. knowlesi (Adams et al., 1992). The first region identified as the ligand-binding domain is RII and the second region that has as yet an unknown function is RVI (FIG. 2). A comparison between EBP2 and EBA-175 showed that EBP2 has little homology with the regions III to V defined for EBA-175. The ORF of the partial gene sequence encoding epb2 does not include the membrane-spanning domain nor the cytoplasmic tail described for EBA-175. The ORF of the partial gene sequence of ebp2 encoded for a molecule of approximately 133 kDa. The molecular mass of EBP2 identified by immunoprecipitation was 130 kDa (Example 5), which suggests that nearly the entire gene sequence has been identified. Subcellular localization studies by IFA demonstrated that EBP2 colocalized with EBA-175 at the apical end of the merozoite. EBA-175 is trafficked to the micronemes, which are organelles localized at the merozoites apical end and are involved in parasite invasion (Sim et al., 1992).

An orthologue of EBA-175 present in P. vivax, that is identified as the Duffy-antigen binding protein is most similar to EBP2-F1. A comparison of EBP2 and the P. vivax DABP region II deduced amino acid sequence showed that DABP region II is more similar to EBP2-F1 (12 out of 13 cysteines are conserved) which is similar to that previously reported for EBA-175 RII-F1 (Adams et al., 1992).

Parasite invasion of erythrocytes is known to occur by different invasion pathways in vitro. Analysis of P. falciparum strains adapted to long-term in vitro culture (Narum et al., 2000, Dolan et al., 1994) has shown that different parasites strains may invade erythrocytes in a sialic acid dependent and sialic acid independent manner. This is generally determined by enzymatically treating erythrocytes with neuraminidase, which cleaves sialic acid residues. It is known that EBA-175 binds sialic acid residues in conjunction with the peptide backbone of glycophorin A (Sim et al., 1994). EBP2 erythrocyte binding was also dependent on sialic acid residues for binding (Example 6). The binding affinity of EBP2 appears greater than EBA-175 since EBP2 was not removed by 150 mM NaCl wash (Example 5). The existence of a family of EBPs broadens the spectrum of phenotypic differences between erythrocytes that that may be utilized by P. falciparum.

In summary, EPB2 is a novel P. falciparum 130 kDa EBP belonging to a family of paralogues of EBA-175. EBP2 also has a ligand-binding domain, identified as RII. EBP2 is localized within the merozoite apex and native protein binds erythrocytes in a sialic acid dependent manner. EBP2 is a malaria vaccine candidate and target for a receptor blocking therapy.

Also provided herein are antibodies to each of the paralogues. In a preferred embodiment of the present invention, the antibodies are specific for each of the paralogues of the P. falciparum binding proteins. In a further preferred embodiment, the antibodies are monoclonal and directed toward paralogues of the erythrocyte binding protein EBA-175 as defined by Camus and Hadley (1985), Sim et al. (1990), and Orlandi et al. (1992).

In another preferred embodiment EBP2 RII specific antibodies that did not cross-react with native EBA-175 were generated using a DNA vaccine. These antibodies recognize a novel 130 kDa protein that bound human erythrocytes in a sialic acid dependent manner. EBP2 RII specific antibodies blocked native EBP2 binding in a concentration dependent manner, which indicated that EBP2 RII was the ligand binding domain.

The inventors have studied whether certain EBA-175 RII paralogues that block EBA-175 binding will inhibit merozoite invasion in vitro. The inventors have also studied whether certain antibodies specific to EBA-175 paralogues have a similar blocking effect on merozoite invasion. It was found that EBP2 RII specific antibodies blocked EBP2 binding to erythrocytes. EBA-175 RII antibody titers correlate with control of parasitemia in an EBA-175 RII Aotus monkey challenge study. Therefore, EBP2 antibodies for inhibition of parasite development in vitro are claimed herein.

The antibodies of the present invention can be polyclonal antibodies or monoclonal antibodies. Antibodies specific for the family of paralogues of *P. falciparum* erythrocyte binding proteins may be administered to a human or animal to passively immunize the human or animal against *P. falciparum* infection, thereby reducing *P. falciparum* related diseases such as malaria. Antibody derived blocking peptides specific for *P. falciparum* erythrocyte binding proteins may be administered to a human or animal to immunize the human or animal against *P. falciparum* infection, thereby reducing *P. falciparum* related diseases such as malaria. The antibodies are also useful as in vitro research tools for studying malaria and for isolating large quantities of *P. falciparum* erythrocyte binding proteins. The antibodies specific for the family of paralogues of *P. falciparum* erythrocyte binding proteins can be used in diagnostic kits to detect the presence and quantity of *P. falciparum* erythrocyte binding proteins, which is diagnostic or prognostic for the occurrence or recurrence of diseases such as malaria. Additionally, the antibody derived blocking peptides that inhibit binding of *P. falciparum* binding to erythrocytes can be used in diagnostic kits to detect the presence and quantity of *P. falciparum* antibodies, which is diagnostic or prognostic for the occurrence of diseases such as malaria.

When labeled isotopically or with other molecules or proteins, the *P. falciparum* antibodies to the family of EBA-175 paralogues are useful in the identification and quantitation of *P. falciparum* utilizing techniques including, but not limited to, positron emission tomography, autoradiography, flow cytometry, radioreceptor binding assays, and immunohistochemistry.

The antibodies and antibody derived blocking peptides of each of the paralogues of the present invention can be isolated from serum or synthesized by chemical or biological methods. For example, the antibodies and antibody derived blocking peptides can be isolated from cell culture, produced by recombinant gene expression or polypeptide synthesis, or derived by in vitro enzymatic catalysis of larger, encompassing polypeptides to yield blocking or neutralizing antibodies or antibody derived blocking peptides. Recombinant techniques include gene amplification from DNA sources using amplification techniques such as the polymerase chain reaction (PCR), and gene amplification from RNA sources using amplification techniques such as reverse transcriptase/PCR. In a preferred embodiment, the antibody derived blocking peptides are produced and analyzed via phage display technology. Phage vectors that may be used in phage display technology include, but are not limited to, λ, M13, MS2, Mu, P4, λgtII, and ϕX174.

The antibodies and antibody derived blocking peptides of the present invention may be labeled directly with a detectable label for identification and quantitation of *P. falciparum* or antibody thereto. Labels for use in immunoassays are generally known to those skilled in the art and include enzymes, radioisotopes, and fluorescent, luminescent and chromogenic substances including colored particles such as colloidal gold and latex beads. Suitable immunoassays include enzyme-linked immunosorbent assays (ELISA) and radioimmunoassays.

Alternatively, the antibodies and antibody derived blocking peptides of the present invention may be labeled indirectly by reaction with labeled substances that have an affinity for immunoglobulin, such as protein A or G or second antibodies. When using secondary antibodies, a suitable immunoassay is an immunoblot or Western blot. Additionally, the antibodies or antibody derived blocking peptides may be conjugated with a second substance and detected with a labeled third substance having an affinity for the second substance conjugated to the antibody. For example, the antibodies or antibody derived blocking peptides maybe conjugated to biotin and the antibody-biotin conjugate detected using labeled avidin or streptavidin. Similarly, the antibodies or antibody derived blocking peptides may be conjugated to a hapten and the antibody-hapten conjugate detected using labeled anti-hapten antibody. These and other methods of labeling antibodies and assay conjugates are well known to those skilled in the art.

When labeled with a detectable biomolecule or chemical, the *P. falciparum* erythrocyte binding protein antibodies and antibody derived blocking peptides described above are useful for purposes such as in vivo and in vitro diagnostics and laboratory research using the methods and assays described below. Various types of labels and methods of conjugating the labels to the polypeptides and antibodies are well known to those skilled in the art. Several specific labels are set forth below.

For example, the antibodies and antibody derived blocking peptides are conjugated to a radiolabel such as, but not restricted to, $^{32}P$, $^{3}H$, $^{14}C$, $^{35}S$, $^{125}I$, or $^{131}I$. Detection of a label can be by methods such as scintillation counting, gamma ray spectrometry or autoradiography.

Bioluminescent labels, such as derivatives of firefly luciferin, are also useful. The bioluminescent substance is covalently bound to the polypeptide or antibody by conventional methods, and the labeled antibody is detected when an enzyme, such as luciferase, catalyzes a reaction with ATP causing the bioluminescent molecule to emit photons of light.

Fluorogens may also be used as labels. Examples of fluorogens include fluorescein and derivatives, phycoerythrin, allo-phycocyanin, phycocyanin, rhodamine, and Texas Red. The fluorogens are generally detected by a fluorescence detector.

The antibodies and antibody derived peptides can alternatively be labeled with a chromogen to provide an enzyme or affinity label. For example, the antibody can be biotinylated so that it can be utilized in a biotin-avidin reaction, which may also be coupled to a label such as an enzyme or fluorogen. Alternatively, the antibodies or antibody derived peptides can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, antibodies and antibody derived peptides may be labeled with colloidal gold for use in immunoelectron microscopy in accordance with methods well known to those skilled in the art.

The paralogues, antibodies and derived blocking peptides described herein are particularly useful for the treatment, prevention, diagnosis and detection of *P. falciparum* infections. The paralogues, antibodies and derived blocking peptides of the present invention may be used for the treatment, prevention, diagnosis or prognosis of *P. falciparum* related diseases such as malaria. Methods of prevention include passive immunization with the paralogues and/or antibodies of the present invention prior to infection by *P. falciparum* to inhibit parasitic infection of erythrocytes. Methods of prevention also include active immunization with the derived blocking peptides of the present invention prior to infection by *P. falciparum* to inhibit parasitic infection of erythrocytes. Methods of treatment include administration of the paralogues, antibodies and/or derived blocking peptides after infection to inhibit the spread of the parasite and ameliorate the symptoms of *P. falciparum* infection. The paralogues, antibodies and derived peptides of the present invention may also be used to detect or quantify *P. falciparum* in a biological sample or specimen or culture media, or used in diagnostic methods and kits, as described below. Results from these tests can be used to predict or diagnose the occurrence or recurrence of *P. falciparum* mediated diseases such as malaria. Paralogues, antibodies and derived peptides of the invention may also be used in production facilities or laboratories to isolate additional quantities of the *P. falciparum* erythrocytic binding proteins and/or paralogues thereof, such as by affinity chromatography, or for the development of peptide agonists or antagonists.

*Plasmodium falciparum* related diseases such as malaria are prevented or treated by administering to a patient suffering from a *P. falciparum* related disease, a pharmaceutical composition containing substantially purified *P. falciparum* erythrocyte binding protein paralogues, peptides thereof and antibodies thereof, *P. falciparum* antibody derived blocking peptides, *P. falciparum* polypeptide agonists or antagonists, or *P. falciparum* polypeptide antisera. Additional prevention and treatment methods include administration of *P. falciparum* erythrocyte binding protein paralogues, peptides thereof and antibodies thereof, *P. falciparum* antibody derived blocking peptides, *P. falciparum* polypeptide antisera, or *P. falciparum* polypeptide receptor agonists and antagonists linked to cytotoxic or anti-parasitic agents.

The paralogues and antibodies specific thereof may be administered to a patient to passively immunize the patient against *P. falciparum* infection, thereby reducing *P. falciparum* related diseases such as malaria. The derived blocking peptides that specifically inhibit binding of *P. falciparum* to a red blood cell may also be administered to a patient to actively immunize the patient against *P. falciparum* infection, thereby reducing *P. falciparum* related diseases such as malaria. Administration of the *P. falciparum* erythrocyte binding protein paralogues, antibodies or derived blocking peptides may occur prior to any signs of *P. falciparum* infection. Such an administration would be important in individuals in areas where *P. falciparum* is endemic, or to individuals planning to travel to endemic areas. Administration of the *P. falciparum* erythrocyte binding protein paralogues, antibodies and derived blocking peptides may also occur after signs of *P. falciparum* infection have surfaced in order to interrupt the life cycle of the *Plasmodium* parasite and inhibit the spread of the organism.

In a preferred embodiment, a vaccine for passive or active immunization against malaria is packaged in a single dosage for immunization by parenteral (i.e., intramuscular, intradermal or subcutaneous) administration. The vaccine is most preferably injected intramuscularly into the deltoid muscle. The vaccine is preferably combined with a pharmaceutically acceptable carrier to facilitate administration. The carrier is usually water or a buffered saline, with or without a preservative. The vaccine may be lyophilized for re-suspension at the time of administration or in solution.

The carrier to which the paralogues, antibody or derived blocking peptides may be conjugated may also be a polymeric delayed release system. Synthetic polymers are particularly useful in the formulation of a vaccine to effect the controlled release of antibody. Microencapsulation of the paralogues, antibody or derived blocking peptide will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly(d,l-lactide-co-glycolide) (PLGA) and other biodegradable polymers.

The preferred dose for human administration of the pharmaceutical composition or vaccine is from 0.01 mg/kg to 10 mg/kg. Based on this range, equivalent dosages for heavier body weights can be determined. The dose should be adjusted to suit the individual to whom the composition is administered and will vary with age, weight and metabolism of the individual. The vaccine may additionally contain stabilizers such as thimerosal (ethyl(2-mercaptobenzoate-S) mercury sodium salt) (Sigma Chemical Company, St. Louis, Mo.) or physiologically acceptable preservatives.

Region II DNA vaccines were constructed using the DNA vaccine backbone VR1020 for the panel of EBPs using standard molecular biological methods. EBP Region II gene inserts were amplified by PCR and verified by restriction enzyme mapping and DNA sequencing of the complete insert (ebp2 and ebp3) or plasmid junctions (ebp4 and ebp5).

Polyclonal anti-sera from groups of Balb/c immunized by DNA vaccination were tested for recognition of *Plasmodium falciparum* blood stage proteins by indirect immunofluorescence antibody test (IFAT) using methanol fixed parasitized erythrocytes.

VM92 cells were transiently transfected with the panel of EBP Region II DNA vaccines as described for EBP2 and culture supernatants were tested for secreted EBP Region II protein by immunoblot using homologous DNA vaccinated mouse antiserum.

TABLE 1 is a summary of EBP2, EBP3, EBP4, and EBP5 region II DNA vaccine construction, expression in vitro and generation of polyclonal anti-EBP2, EBP3, EBP4, and EBP5 antisera in vivo.

TABLE 1

| Protein identifier | Gene identifier | Chromosome location | EBP Region RII DNA vaccine produced | Mice immunized | IFAT staining results | Immunoblot results |
| --- | --- | --- | --- | --- | --- | --- |
| EBA-175 or SABP[1] | eba-175 (or ebp1) | 7 | Yes | Yes | Positive | Positive |
| EBP2 | ebp2 | 13 | Yes | Yes | Positive | Positive |
| EBP3 | ebp3 | 13 | Yes | Yes | Negative | Negative |
| EBP4 | ebp4 | 4 | Yes | Yes | Negative | Negative |
| EBP5 | ebp5 | 1 | Yes | Yes | Negative | Negative |

The paralogues and antibodies of the present invention may also be used for the detection of *P. falciparum* peptides in biological samples or culture media. There are many techniques known in the art for detecting a component such as a polypeptide in a mixture and/or measuring its amount.

Immunoassays, which employ antibodies that bind specifically to the polypeptide of interest, are one of the better known measurement techniques. Classical methods involve reacting a sample containing the polypeptide with a known excess amount of antibody specific for the polypeptide, separating bound from free antibody, and determining the amount of one or the other. Often the antibody is labeled with a reporter group to aid in the determination of the amount of bound analyte as described above. The reporter group or "label" is commonly a fluorescent or radioactive group or an enzyme.

An immunoassay is performed for the detection of *P. falciparum* in a sample as follows:

A sample is collected or obtained using methods well known to those skilled in the art. The sample containing the *P. falciparum* polypeptides to be detected may be obtained from an culture media or any biological source. Examples of biological sources include blood serum, blood plasma, urine, spinal fluid, fermentation fluid, lymph fluid, tissue culture fluid and ascites fluid. The sample may be diluted, purified, concentrated, filtered, dissolved, suspended or otherwise manipulated prior to immunoassay to optimize the immunoassay results.

To detect *P. falciparum* polypeptides, the sample is incubated with one or more of the *P. falciparum* erythrocyte binding protein paralogue antibodies of the present invention. The antibody may be labeled or conjugated to a solid phase bead or particle as also described herein. The labeled antibody is then detected using methods well known to those skilled in the art. The term "detecting" or "detected" as used herein means using known techniques for detection of biologic molecules such as immunochemical or histological methods. Such methods include immunological techniques employing monoclonal or polyclonal antibodies to the peptides, such as enzyme linked immunosorbant assays, radioimmunoassay, chemiluminescent assays, or other types of assays involving antibodies known to those skilled in the art.

Current binding assay technology benefits from the diversity of detection systems developed that use enzyme-catalyzed chromogenic reactions, radionuclides, chemiluminescence, bioluminescence, fluorescence, fluorescence polarization and a variety of potentiometric and optical biosensor techniques.

Binding assays rely on the binding of analyte by analyte receptors to determine the concentrations of analyte in a sample. Analyte-receptor assays can be described as either competitive or non-competitive. Non-competitive assays generally utilize analyte receptors in substantial excess over the concentration of analyte to be determined in the assay. Sandwich assays are examples of non-competitive assays, that comprise one analyte receptor frequently bound to a solid phase and a second analyte receptor labeled to permit detection. The analyte first binds to the analyte receptor bound to a solid phase and the second labeled analyte receptor is then added to facilitate quantitation of the analyte. Bound analyte can easily be separated from unbound reagents, such as unbound labeled first analyte receptors, due to the use of an analyte receptor bound to a solid phase.

Competitive assays generally involve a sample suspected of containing analyte, an analyte-analogue conjugate, and the competition of these species for a limited number of binding sites provided by the analyte receptor. Competitive assays can be further described as being either homogeneous or heterogeneous. In homogeneous assays all of the reactants participating in the competition are mixed together and the quantity of analyte is determined by its effect on the extent of binding between analyte receptor and analyte-conjugate or analyte analogue-conjugate. The signal observed is modulated by the extent of this binding and can be related to the amount of analyte in the sample. U.S. Pat. No. 3,817,837 describes such a homogeneous, competitive assay in which the analyte analogue conjugate is a analyte analogue-enzyme conjugate and the analyte receptor, in this case a paralogue of EBA-175 or an antibody thereof, is capable of binding to either the analyte or the analyte analogue. The binding of the paralogue or antibody to the analyte analogue-enzyme conjugate decreases the activity of the enzyme relative to the activity observed when the enzyme is in the unbound state. Due to competition between unbound analyte and analyte analogue-enzyme conjugate for analyte-receptor binding sites, as the analyte concentration increases the amount of unbound analyte analogue-enzyme conjugate increases and thereby increases the observed signal. The product of the enzyme reaction may then be measured kinetically using a spectrophotometer.

Heterogeneous, competitive assays require a separation of analyte analogue conjugate bound to analyte receptor from the free analyte analogue conjugate and measurements of either the bound or the free fractions. Separation of the bound from the free may be accomplished by removal of the analyte receptor and anything bound to it from the free analyte analogue conjugate by immobilization of the analyte receptor on a solid phase or precipitation. The amount of the analyte analogue conjugate in the bound or the free fraction can then be determined and related to the concentration of the analyte in the sample. Normally the bound fraction is in a convenient form, for example, on a solid phase, so that it can be washed, if necessary, to remove remaining unbound analyte analogue conjugate and the measurement of the bound analyte analogue conjugate or related products is facilitated. The free fraction is normally in a liquid form that is generally inconvenient for measurements. If multiple analytes are being determined in a single assay, the determination of the free fraction of analyte analogue conjugate for each analyte is made impossible if all are mixed in a single liquid unless the responses of the individual analyte analogue conjugates can be distinguished in some manner. However, detecting the free fraction of analyte analogue conjugate in assays that are visually interpreted is a distinct advantage because the density of the color developed in such assays is generally proportional to the analyte concentration over much of the range of analyte concentration.

In a preferred embodiment, the method for detecting and characterizing *P. falciparum* polypeptides comprises taking a sample from a protein production lot. A determination of the presence of the immunodominant polypeptides can then be made using assay techniques that are well known to those skilled in the art and include methods such as Western blot analysis, radioimmunoasssay and ELISA assays.

In a second preferred embodiment, the method for detecting *P. falciparum* polypeptides comprises taking biological samples, such as fluids and tissues, from a mammal for the diagnosis or prognosis of malaria. The sample is preferably obtained from the blood, cerebrospinal fluid, urine or tissues of a mammal, preferably a human or simian. A determination of the presence of the immunodominant polypeptides can then be made using assay techniques that are well known to those skilled in the art and include methods such as Western blot analysis, radioimmunoasssay and ELISA assays.

A kit for detecting the presence and quantity of *P. falciparum* paralogues, antibodies thereof and/or derived peptides is also provided. The kit can be in any configuration well known to those of ordinary skill in the art and is useful performing one or more of the methods described herein for the detection of *P. falciparum* in biological samples or for the detection or monitoring of *P. falciparum* infection in a patient or carrier. The kits are convenient in that they supply many if not all of the essential reagents for conducting an assay for the detection of *P. falciparum* in a biological sample. The reagents may be premeasured and contained in a stable form in vessels or on a solid phase in or on which the assay may be performed, thereby minimizing the number of manipulations carried out by the individual conducting the assay. In addition, the assay may be performed simultaneously with a standard that is included with the kit, such as a predetermined amount of a paralogue of the invention, or antigen or antibody thereof, so that the results of the test can be validated or measured.

In one embodiment, the kit preferably contains one or more *Plasmodium falciparum* erythrocyte binding protein antibodies that can be used for the detection of *P. falciparum* binding proteins in a sample. The kit can additionally contain the appropriate reagents for binding or hybridizing the antibodies to their respective *P. falciparum* binding molecules or ligands in the sample as described herein and reagents that aid in detecting the bound peptides. The kit may additionally contain equipment for safely obtaining the sample, a vessel for containing the reagents, a timing means, a buffer for diluting the sample, and a calorimeter, reflectometer, or standard against which a color change may be measured.

In another preferred embodiment, the reagents, including the antibody, are lyophilized, most preferably in a single vessel. Addition of aqueous sample to the vessel results in solubilization of the lyophilized reagents, causing them to react. Most preferably, the reagents are sequentially lyophilized in a single container, in accordance with methods well known to those skilled in the art that minimize reaction by the reagents prior to addition of the sample.

The assay kit includes but is not limited to reagents to be employed in the following techniques; competitive and non-competitive assays, radioimmunoassay, bioluminescence and chemiluminescence assays, fluorometric assays, sandwich assays, immunoradiometric assays, dot blots, enzyme linked assays including immunoblots and ELISAs, and immunocytochemistry. Materials used in conjunction with these techniques include, but are not limited to, microtiter plates, antibody coated strips or dipsticks for rapid monitoring of urine or blood. For each kit, the range, sensitivity, precision, reliability, specificity and reproducibility of the assay are established. Intraassay and interassay variation is established at 20%, 50% and 80% points on the standard curves of displacement or activity.

In a further preferred embodiment, the assay kit uses immunoblot techniques and provides instructions, *P. falciparum* polypeptides, and *P. falciparum* erythrocyte binding protein antibodies conjugated to a detectable molecule. The kit is useful for the measurement of *P. falciparum* in biological fluids and tissue extracts of animals and humans with and without malaria, as well as in culture media.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. All patents and references disclosed herein are incorporated by reference.

EXAMPLE 1

Materials and Methods for Detecting *P. falciparum* EBPs

Genomic Database

The sequence data for *P. falciparum* chromosome 13 was obtained from The Sanger Centre website at Worldwide Web at sanger.ac.uk/Projects/P_falciparum/. Sequencing of *P. falciparum* chromosome 13 was accomplished as part of the Malaria Genome Project with support by The Wellcome Trust.

Parasites

*Plasmodium falciparum* 3D7 strain (clone of NF54, Amsterdam Airport, human challenge strain) and FVO strain (Aotus adapted) were maintained as previously reported (Vernes et al., 1984). When appropriate, schizonts were purified on Percoll density gradient. The 3D7 parasites were metabolically labeled with TRAN$^{35}$S-LABEL™ (ICN Radiochemicals, Irvine, Calif.) as previously described (Sim et al., 1994b). Essentially 2×10$^8$ parasites in 10 ml RPMI-1640 culture media deficient in methionine and cysteine were incubated with 1 mCi TRAN$^{35}$S-LABEL™ for 4 hours for parasite-cell pellets and 16-24 hours for culture supernatants. Parasitized erythrocytes for preparation of schizont extracts were washed twice in RPMI-1640 and cell pellets were frozen at −70° C. For the collection of labeled parasite proteins, cells were removed by centrifugation (1 min. at 20,000×g) and supernatants were stored at −70° C.

RT-PCR Analysis

Aliquots of purified mRNA, isolated from purified schizont infected erythrocytes using a mRNA isolation kit (Stratagene, La Jolla, Calif.), were stored precipitated in ethanol with 3M sodium acetate at −70° C. The mRNA was treated with DNAase to ensure that it was free of genomic DNA; the absence of DNA was confirmed by the lack of amplification in RT-PCR studies in the absence of reverse transcriptase. First strand cDNA transcripts were prepared using a poly dT primer from a cDNA CYCLE™ kit (Invitrogen, Carlsbad, Calif.). This first strand product was amplified by PCR using the oligonucleotide forward primer 5' CAAGGAGAATGTATGGAAAGTA 3' (SEQ ID NO: 6) and reverse primer 5' ATCTTCATATTCATTTGGACTCT 3' (SEQ ID NO: 7). The PCR amplified product was detected by ethidium bromide staining a 1% agarose gel.

EBP2 DNA Sequence Analysis and Plasmid Vaccine Construction

*P. falciparum* EBP2 RII (amino acids 147-762, 1848bp) was amplified using AdvanTaq Plus™ DNA polymerase (Clontech, Palo Alto, CA) from 100 ng of 3D7 genomic DNA using the forward primer 5' ATGCGGATC-CCAATATACGTTTATACAGAAACGTACTC 3' (SEQ ID N0: 8) and reverse primer 5' ATGCGGATCCT-CATATATCGTGTTTTGTTTTAGG 3' (SEQ ID NO: 9) which both contained a BamHI site and the reverse primer contained an additional internal stop codon for cloning into the shuttle vector PCR-Script™ as described by the manufacturer's instructions (Stratagene, La Jolla, CA). The ebp2 RII gene fragment excised with BamHI and cloned into the expression plasmid vector VR1020 (identified as pEBP2-RII). The VR 1020 plasmid vector utilizes the human cytomegalovirus promoter and intron A, and human tissue plasminogen activator as the secretory signal and the bovine growth hormone transcriptional terminator/polyadenylation signal (Hartikka et al., 1996). A clone was selected for correct orientation by restriction-enzyme mapping. Both the forward and reverse strands of the ebp2 RII ORF were sequenced using primers off of the vector and primers based on the cloned sequences (Veritas, Inc., Rockville, Md.). Human melanoma cells (UM449), were transiently transfected with the plasmids pEBP2RII, 3D7 encoded pEBA-175RII and VR1020 plasmid with Lipofectamine™ following the manufacture's protocol (Life Technologies, Gaithersburg, Md.). Secretion of RII protein in culture supernatants was confirmed by Western blot. Plasmids were prepared for immunizations using an EndoFree Plasmid Giga kit (Qiagen, Valencia, Calif.). Purity was gauged by UV spectroscopy (260 nm/280 nm was between 1.70 and 1.90), agarose gel electrophoresis showing predominately supercoiled plasmid and endotoxin levels (<10 EU/mg) were detected using the *Limulus amebocyte* assay. The ebp2 RVI was amplified by PCR as above except used Vent DNA polymerase (New England BioLabs, Beverly, Mass.) using the forward primer 5' TCTAGAGATACTAAAAGAGTAAGG 3' (SEQ ID NO: 10) and reverse primer 5' TGATTGACCCTCGCTTTTAAAAC 3' (SEQ ID NO: 11). The PCR amplified fragment was gel purified and both the forward and reverse strands were sequenced directly (Veritas, Inc.).

Animals and Immunizations

All animal studies were done in compliance with protocols approved by Animal Care and Use Committees. BALB/c mice were inoculated intradermally with a 29 gauge needle at two sites in the tail with a total of 50 µg VR1020 (empty vector), pEBP2RII in 50 µl PBS. The mice were inoculated on days 0, 21, 42 and bled approximately two weeks after each immunization. A fourth dose was administered approximately three months after the third dose and bled two weeks later. Pooled sera were assessed for antibodies to parasitized erythrocytes by IFA.

Immunoprecipitation, Immunoblotting and Immunofluorescence Assay

Aliquots of approximately $2 \times 10^8$ parasitized RBCs that had been metabolically labeled were extracted in buffer containing 1% Triton X-100 (Sigma, St. Louis, Mo.) (Narum et al., 1994). Schizont infected erythrocyte lysates (50 to 75 µl) were immunoprecipitated with mouse serum or purified rabbit IgG coupled to Protein G (Pharmacia Biotech., Uppsala, Sweden) and the precipitates were washed as previously described using a buffer containing Triton X-100 (Deans and Jeans, 1987; Narum et al., 1994). The labeled proteins were resolved by SDS-PAGE and detected and/or quantified with a phosphoimager (BioRad Molecular Imager FX, Hercules, Calif.). Immunoblots were prepared essentially as described previously (Narum et al) using EBP specific antisera. IFA on thin films containing schizont-infected erythrocytes used mouse anti-EBP2 sera (1/50 dilution in PBS-1% FCS) and rabbit anti-EBA-175 RII IgG (2 µg/ml in buffer) were co-incubated for 1 hour in a moisture chamber. After washing in PBS, the parasitized cells were co-incubated with species specific fluorescein or Alexa™ 546 labeled secondary antibodies (Kirkegaard & Perry Laboratories, Inc., Gaithersburg, Md. and Molecular Probes, Eugene, Oreg., respectively). The same microscope field was photographed using excitation for both fluorescein and Alexa 546. Alexa 546 emission appears orange.

EBPs Binding Studies and Blocking of Binding to Erythrocytes

Metabolically labeled parasite culture supernatant containing [$^{35}$S]-metabolically labeled EBPs was used for erythrocyte binding assays as previously described by Camus and Hadley (1985) or Sim et al. (1994). Briefly, two samples were prepared containing 1 ml [$^{35}$S]-labeled culture supernatant and $2 \times 10^9$ packed erythrocytes that were incubated for 45 minutes at room temperature while rocking for binding to occur. To one vial, the erythrocytes were pelleted, washed thrice in PBS and the erythrocyte pellet was extracted in 500 µl 1% Triton X-100 extraction buffer. EBP bound erythrocyte lysates were immunoprecipitated using 80 µl extract with antigen specific antisera or control sera coupled to Protein G. The other sample was divided into four parts and the EBPs were eluted from erythrocytes with 9 µl of RPMI 1640, 1.5 M NaCl, 10% FCS, and 2 mM phenymethylsulfonyl fluoride as previously described (Sim et al., 1994). Elution material was pooled and diluted 15-fold in PBS-1% FCS and equal volumes were immunoprecipitated with antigen specific antisera or control sera as above. Gels were dried and quantified with a phosphoimager (BioRad Molecular Imager FX, Hercules, Calif.).

Blocking of binding was performed by pre-incubating a titration of EBP2 specific antisera with 100 µl [$^{35}$S]-labeled culture supernatant for 45 minutes and then $2 \times 10^8$ erythrocytes were added and incubated for 30 minutes at room temperature while rocking. Erythrocyte pellets were washed thrice with PBS, extracted in 50 µl 1% Triton X-100 extraction buffer, immunoprecipitated with EBP2 antisera coupled to Protein G and analyzed as above. Blocking of binding was calculated as follows: (control−experiment/control)×100. The "control" is the counts from EBP2 bound to erythrocytes in the presence of control sera.

Neuraminidase Treatment of Erythrocytes:

Human blood was collected in a final 10% citrate phosphate dextrose solution, washed and treated with 0.2 Upper $1 \times 10^9$ erythrocytes *Vibrio cholerae* neuraminidase (Gibco BRL, Gaithersburg, Md.) as previously described (Liang et al 2000).

EXAMPLE 2

Expression of EBP2 in Parasitized Erythrocytes

To examine whether ebp2 was transcribed a mRNA transcript was detected with RT-PCR. Parasite mRNA isolated from 3D7 schizont-infected erythrocytes was used for first strand synthesis with random primers or with a poly dT primer and then PCR amplified with an ebp2 primer pair or eba-175 primer pair as a control. Appropriate size DNA fragments were detected on an ethidium bromide stained agarose gel for ebp2 and eba-175. Using genomic 3D7 DNA, ebp2 RII was amplified by PCR and cloned into a naked DNA vaccine plasmid (Hartikka et al., 1996). Both the forward and reverse strands of the DNA fragment were sequenced. A single point nucleotide change at position 1654 (A to G) encoded an amino acid substitution from Asn to Asp. This single amino acid difference is the result of a PCR-introduced artifact.

Recombinant EBP2 RII and EBA-175 RII derived from supernatants by transient transfection of UM449 cells were immunoblotted with specific antisera generated as below.

A western blot of secreted *P. falciparum* 3D7 EBP2 RII (A) and 3D7 EBA-175 RII (B) proteins showed expression of EBP2 in vitro and specificity of EBP2 and EBA-175 antibodies. UM449 cells were transiently transfected with naked DNA plasmid pEBP2 RII and run in lane 1. VR1020 (Vical, San Diego, Calif.) control was run in lane 2. pEBA-175 RII was run in lane 3. EBP2 RII and EBA-175 RII recombinant proteins were detected by RII specific mouse antibodies. EBP2 RII and EBA-175 RII anti-sera were specific for self and showed no detectable cross-reactivity.

Pooled immune sera from BALB/c mice immunized with the EBP2 RII DNA vaccine and empty vector as control were tested for the presence of EBP2 RII specific antibodies by Immunofluorescence assay (IFA). The IFA showed co-localization of EBP2 and EBA-175 within *P. falciparum* schizont infected erythrocyte. EBP2 was stained with mouse anti-EBP2 RII sera and EBA-175 was stained with rabbit anti-EBA-175 RII IgG. Both primary and secondary antibody controls were negative for staining. Cells were magnified 1000-fold. EBP2 RII antisera recognized 3D7 and FVO schizont-infected erythrocytes and gave a punctate apical pattern of fluorescence. The reciprocal end-point titer of pooled immune sera was 1600 on 3D7 parasitized erythrocytes by IFA. The subcellular pattern of apical fluorescence was compared to EBA-175 using EBA-175 RII specific antibodies generated in rabbits. The results showed that EBP2 and EBA-175 colocalized to the same subcellular location within the merozoite's apex.

EXAMPLE 3

EBP2 RII Specific Antibodies Recognize a 130 kDa *P. falciparum* Protein

To determine the molecular mass of EBP2 [$^{35}$S]metabolically labeled *P. falciparum* 3D7 strain schizont-infected erythrocyte lysates were incubated with EBP2 RII specific antibodies coupled to Protein G-sepharose. [$^{35}$S]labeled *P. falciparum* schizont-infected erythrocyte lysate were immunoprecipitated and human erythrocyte bound [$^{35}$S]labeled EBP2 were detected from [$^{35}$S]-labeled parasite culture supernatants. EBA-175 specific polyclonal rabbit IgG was included as a control. Results were obtained with EBP2 specific polyclonal sera or control and EBA-175 specific polyclonal IgG and control. [$^{35}$S]-labeled EBP2 and EBA-175 were immunoprecipitated from lysates of erythrocytes with bound EBPs. [$^{35}$S]-labeled EBP2 and EBA-175 were eluted off human erythrocytes with 1M NaCl and then immunoprecipitated with EBP2 or EBA-175 specific antibodies. Mouse and rabbit adjuvant controls and molecular mass markers were employed. The molecular mass of processed or degraded forms of EBP2 were: a, 117.2; b, 92.2; c, 85.8; and d, 697 kDa. EBP2 RII antibodies immunoprecipitated a 130 kDa molecule as determined by SDS-PAGE under reducing conditions. The theoretical molecular mass of the ebp2 ORF is 133,018 Daltons hence the observed molecular mass is similar to the theoretical. EBA-175 was also immunoprecipitated with EBA-175 RII specific rabbit polyclonal IgG as a control. The EBP2 RII antisera did not immunoprecipitate the abundantly labeled EBA-175 nor did EBA-175 RII antibodies immunoprecipitate EBP2.

EXAMPLE 4

EBP2 Binds Human Erythrocytes

It was determined that EBP2 bound to human erythrocytes by using [$^{35}$S]-labeled *P. falciparum* culture supernatants that contained *P. falciparum* proteins released during maturation of schizogony in vitro. Immunoprecipitation of human erythrocyte lysates or eluates prepared as described in Materials and Methods showed that EBP2 bound human erythrocytes. EBA-175 specific rabbit IgG and rabbit control IgG were included in the analysis. The binding affinity of EBP2 was greater than that of EBA-175. Immunoprecipitation of erythrocyte lysates that were prepared by incubating erythrocytes and [$^{35}$S]-labeled *P. falciparum* culture supernatants, washed with PBS and incubated with mouse EBP2 RII and rabbit EBA-175 RII specific antibodies showed that EBP2 was not removed by the PBS while EBA-175 was removed. EBP2 RII antisera predominately immunoprecipitated a 69.7 kDa fragment although other larger fragments were also detected but were only weakly visible. The 69.7 kDa fragment identified in the culture supernatant appears to be a processed or degraded product of the larger 130 kDa form of EBP2 identified in schizont-infected erythrocyte lysates. Analysis of erythrocyte eluates obtained by immunoprecipitation showed similar binding patterns for EBP2, although the intensity of the other fragments by this approach was greater. The EBP2 fragments were 117.2, 92.2, 85.8 and 69.7 kDa. EBA-175 was detected using these conditions as previously reported (Orlandi et al., 1990).

EXAMPLE 5

EBP2 RII Specific Antibodies Block EBP2 Erythrocyte Binding

To determine whether EBP RII antibodies blocked EBP2 binding to erythrocytes, EBP2 immune sera was titrated with [$^{35}$S]-labeled *P. falciparum* culture supernatants, which was then incubated with human erythrocytes, pelleted, washed and extracted in extraction buffer. Control antisera was at a single dilution of 1/10. Equal volumes of erythrocyte lysate were immunoprecipitated with EBP2 specific polyclonal antibodies. Immunoprecipitation of the erythrocyte lysates demonstrated that EBP2 RII specific antibodies blocked EBP2 binding to human erythrocytes (FIG. 6). The $ED_{50}$ blocking titer was between 1/160 and 1/640.

EXAMPLE 6

EBP2 Binding to Human Erythrocytes is Dependent on Sialic Acid Residues

Human erythrocytes were used in untreated form or were enzymatically treated with neuraminidase, which cleaves sialic acid residues. The erythrocytes were then incubated with [$^{35}$S]-labeled *P. falciparum* culture supernatants. Red blood cells (RBCs) were pelleted, washed and extracted in extraction buffer. Equal volumes of erythrocyte lysate were immunoprecipitated with EBP2 specific polyclonal antibodies. EBP2 bound the untreated erythrocytes. Human erythrocytes devoid of sialic acid residues (i.e., neuraminidase treated erythrocytes) did not bind the 69.7 kDa fragment of EBP2. The sialic acid binding results were similar when we tested for EBP2 binding using an EBA-175 erythrocyte binding assay.

EXAMPLE 7

Preparation of Vaccines Using EBP3

DNA vaccine that encoded region II of EBP3 was constructed similarly to EBP2 region II. Forward primer for EBP3: 5' ATGC GGA TCC GAA AAG AAT AAA TTT ATT GAC ACT 3' BamHI (SEQ ID NO: 12); Reverse primer for EBP3: 5' ATGC GGA TCC TCA AGG AAA. CAC ATT CGT TTT TAT AGG 3' BamHI (SEQ ID NO: 13). Mice were immunized and polyclonal immune sera were tested for recognition of parasite proteins by IFAT on methanol fixed parasitized erythrocytes. The results are shown in the Table 1 above. The IFAT results were all negative for detection of an expressed parasite protein except for the novel protein EBP2. EBA-175 was used as a positive control in these studies. EBP3 polyclonal immune was also tested by immunoblot against supernatant collected from VM92 cells transiently transfected individually with the EBP DNA vaccine. The results were all negative except for EBP2 for self-recognition of a transiently expressed region II fragment of EBP2. Although the results for EBP3 was negative here, these studies do not exclude the expression of this protein in erythrocytic stage parasites or in other parasite stages e.g., sporozoite, exo-erythrocytic, or sexual stage parasites.

EXAMPLE 8

Preparation of Vaccines Using EPB4

DNA vaccine that encoded region II of EBP4 was constructed by directly cloning EBP4 into the DNA vaccine VR1020. Specific forward and reverse primers with BamHI restriction sites were used to PCR amplify from genomic (*P. falciparum*) DNA (FIG. 2) using standard molecular biological techniques that are known in the art. Forward primer for EBP4: 5' ATGC GGA TCC AAT CTG AAA GCT CCA AAT GCT AAA TCC 3'BamHI (SEQ ID NO: 14); Reverse primer for EBP4: 5'ATGC GGA TCC TCA TAT AGG AAA CAC ATT CGT TTT TAT AGG 3'BamHI (SEQ ID NO: 15). Mice were immunized and polyclonal immune sera were tested for recognition of parasite proteins by IFAT on methanol fixed parasitized erythrocytes. The results are shown in the Table 1 above. The IFAT results were all negative for detection of an expressed parasite protein except for the novel protein EBP2. EBA-175 was used as a positive control in these studies. EBP4 polyclonal immune was also tested by immunoblot against supematant collected from VM92 cells transiently transfected individually with the EBP DNA vaccine. The results were all negative except for EBP2 for self-recognition of a transiently expressed region II fragment of EBP4. Although the results for EBP4 was negative here, these studies do not exclude the expression of this protein in erythrocytic stage parasites or in other parasite stages such as sporozoite, exo-erythrocytic, or sexual stage parasites.

EXAMPLE 9

Preparation of Vaccines Using EPB5

DNA vaccine that encoded region II of EBP5 was constructed by directly cloning EBP5 into the DNA vaccine VR 1020. Specific forward and reverse primers with BamHI restriction sites were used to PCR amplify from genomic (*P. falciparum*) DNA (FIG. 2) using standard molecular biological techniques that are known in the art. Forward primer for EBP5: 5' ATGC GGA TCC AAT AGA AAT AGT TTT GTT CAA 3'BamHI (SEO ID NO: 16); Reverse pnmer for EBP5: 5'ATGC GGA TCC TCA TGA GTC TAT AGA TAA CAT TTC 3'BamHI (SEQ ID NO: 17). Mice were immunized and polyclonal immune sera were tested for recognition of parasite proteins by IFAT on methanol fixed parasitized erythrocytes. The results are shown in the Table 1 above. The IFAT results were all negative for detection of an expressed parasite protein except for the novel protein EBP2. EBA-175 was used as a positive control in these studies. EBP5 polyclonal immune was also tested by immunoblot against supematant collected from VM92 cells transiently transfected individually with the EBP DNA vaccine. The results were all negative except for EBP2 for self-recognition of a transiently expressed region II fragment of EBP2. Although the results for EBP5 was negative here, these studies do not exclude the expression of this protein in erythrocytic stage parasites or in other parasite stages such as sporozoite, exo-erythrocytic, or sexual stage parasites.

Modifications and variations of the present method will be obvious to those skilled in the art from the foregoing detailed description. Such modifications and variations are intended to come within the scope of the appended claims. All patents, patent applications and publications cited in this application are herein incorporated by reference as if each were incorporated individually.

REFERENCES

Adams, J. H., Hudson, D. E., Torii, M., Ward, G. E., Wellems, T. E., Aikawa, M., Miller, L. H. "The Duffy receptor family of *Plasmodium knowlesi* is located within the micronemes of invasive malaria merozoites." *Cell.* 63: 141-153 (1990).

Adams, J. H., Sim, B. K. L., Dolan, S. A., Fang, X., Kaslow, D. C., Miller, L. H. "A family of erythrocyte binding proteins of malaria parasites." *Proc. Natl. Acad. Sci.* 89: 7085-7089 (1992).

Camus, D., and T. J. Hadley. A *Plasmodium falciparum* antigen that binds to host erythrocytes and merozoites. Science. 1985; 230, no. 4725:553.

Deans, J. A., and W. C. Jeans. 1987. Structural studies on a putative protective *Plasmodium knowlesi* merozoite antigen. Molecular Biochemical Parasitology. 26:155-166.

Dolan, S. A., J. L. Proctor, D. W. Alling, Y. Okubo, T. E. Wellems, and L. H. Miller. 1994. Glycophorin B as an EBA-175 independent *Plasmodium falciparum* receptor of human erythrocytes. Mol Biochem Parasitol. 64:55-63.

Fang, X., Kaslow, D. C., Adams, J. H., Miller, L. H. "Cloning of the *Plasmodium vivax* Duffy receptor." *Mol. Biochem. Parasitol.* 44: 125-132 (1991).

Hartikka, J., M. Sawdey, F. Cornefert-Jensen, M. Margalith, K. Barnhart, M. Nolasco, H. L. Vahlsing, J. Meek, M. Marquet, P. Hobart, J. Norman, and M. Manthorpe. 1996. An improved plasmid DNA expression vector for direct injection into skeletal muscle. Hum Gene Ther. 7:1205-17.

Horuk, R., C. E. Chitnis, W. C. Darbonne, T. J. Colby, A. Rybicki, T. J. Hadley, and L. H. Miller. 1993. A receptor for the malarial parasite *Plasmodium vivax*: the erythrocyte chemokine receptor. Science. 261:1182-4.

Narum, D. L., and A. W. Thomas. 1994. Differential localization of full-length and processed forms of PF83/AMA-1 an apical membrane antigen of *Plasmodium falciparum* merozoites. Mol Biochem Parasitol. 67:59-68.

Narum, D. L., J. D. Haynes, S. Fuhrmann, K. Moch, H. Liang, S. L. Hoffman, and B. K. Sim. 2000. Antibodies against the *plasmodium falciparum* receptor binding domain of EBA-175 block invasion pathways that Do not involve sialic acids [In Process Citation]. Infect Immun. 68:1964-6.

Orlandi, P. A., B. K. Sim, J. D. Chulay, and J. D. Haynes. 1990. Characterization of the 175-kilodalton erythrocyte binding antigen of *Plasmodium falciparum*. Mol Biochem Parasitol. 40:285-94.

Orlandi, P. A., Klotz, F. W. and Haynes, J. D. "A malaria invasion receptor, the 175-kilodalton erythrocyte binding antigen of *Plasmodium falciparum* recognizes the terminal neu5Ac(α2-3)gal-sequences of glycophorin A." *J. Cell Biol.* 116: 901-909 (1992).

Sim, B. K., P. A. Orlandi, J. D. Haynes, F. W. Klotz, J. M. Carter, D. Camus, M. E. Zegans, and J. D. Chulay. Primary structure of the 175K *Plasmodium falciparum* erythrocyte binding antigen and identification of a peptide which elicits antibodies that inhibit malaria merozoite invasion. J Cell Biol. 1990; 111, no. 5 Pt 1:1877-1884.

Sim, B. K., T. Toyoshima, J. D. Haynes, and M. Aikawa. 1992. Localization of the 175-kilodalton erythrocyte binding antigen in micronemes of *Plasmodium falciparum* merozoites. Mol Biochem Parasitol. 51:157-9.

Sim, B. K. L., Chitnis, C. E., Wasniowska, K., Hadley, T. J., Miller, L. H. "Receptor and ligand domains for invasion of erythrocytes by *Plasmodium falciparum*. Science. 264: 1941-1944. (1994).

What is claimed is:

1. A pharmaceutical composition comprising a pharmaceutically acceptable carrier and an isolated polypeptide comprising P. falciparum erythrocyte binding protein-2 (EBP2) Region II (RII). the amino acid sequence of which is amino acids 147 to 762 of SEQ ID NO: 1.

2. The pharmaceutical composition of claim 1, wherein the polypeptide comprises P. falciparum erythrocyte binding protein-2 (EBP2), the amino acid sequence of which is SEQ ID NO:1.

3. The pharmaceutical composition of claim 1, further comprising an isolated sialic acid binding protein (SABP) binding domain polypeptide in an amount sufficient to induce a protective immune response to Plasmodium falciparum merozoites in a mammal.

4. An isolated polypeptide comprising P. falciparum erythrocyte binding protein-2 (EBP2) Region II (RII), the amino acid sequence of which is amino acids 147 to 762 of SEQ ID NO:1.

5. The isolated polypeptide of claim 4, wherein the polypeptide comprises P. falciparum erythrocyte binding protein-2 (EBP2), the amino acid sequence of which is SEQ ID NO:1.

6. A method for inducing an immune response to Plasmodium falciparum merozoites in a patient, the method comprising administration to the patient of an immunologically effective amount of the pharmaceutical composition of claim 1.

7. A method for inducing an immune response to Plasmodium falcitarum merozoites in a patient, the method comprising administration to the patient of an immunologically effective amount of the pharmaceutical composition of claim 2.

8. A method for inducing an immune response to Plasmodium falciparum merozoites in a patient, the method comprising administration to the patient of an immunologically effective amount of the pharmaceutical composition of claim 3.

* * * * *

SEQUENCE LISTING

<160> NUMBER OF SEQ ID NOS: 18

<210> SEQ ID NO 1
<211> LENGTH: 1143
<212> TYPE: PRT
<213> ORGANISM: Plasmodium falciparum

<400> SEQUENCE: 1

```
Thr Asn Lys Leu Tyr Ile Met Lys Gly Tyr Phe Asn Ile Tyr Phe Leu
 1               5                  10                  15

Ile Pro Leu Ile Phe Leu Tyr Asn Val Ile Arg Ile Asn Glu Ser Ile
            20                  25                  30

Ile Gly Arg Thr Leu Tyr Asn Arg Gln Asp Glu Ser Ser Asp Ile Ser
        35                  40                  45

Arg Val Asn Ser Pro Glu Leu Asn Asn Asn His Lys Thr Asn Ile Tyr
    50                  55                  60

Asp Ser Asp Tyr Glu Asp Val Asn Asn Lys Leu Ile Asn Ser Phe Val
 65                  70                  75                  80

Glu Asn Lys Ser Val Lys Lys Arg Ser Leu Ser Phe Ile Asn Asn
                85                  90                  95

Lys Thr Lys Ser Tyr Asp Ile Ile Pro Pro Ser Tyr Ser Tyr Arg Asn
            100                 105                 110

Asp Lys Phe Asn Ser Leu Ser Glu Asn Glu Asp Asn Ser Gly Asn Thr
        115                 120                 125

Asn Ser Asn Asn Phe Ala Asn Thr Ser Glu Ile Ser Ile Gly Lys Asp
130                 135                 140

Asn Lys Gln Tyr Thr Phe Ile Gln Lys Arg Thr His Leu Phe Ala Cys
145                 150                 155                 160

Gly Ile Lys Arg Lys Ser Ile Lys Trp Ile Cys Arg Glu Asn Ser Glu
                165                 170                 175

Lys Ile Thr Val Cys Val Pro Asp Arg Lys Ile Gln Leu Cys Ile Ala
            180                 185                 190

Asn Phe Leu Asn Ser Arg Leu Glu Thr Met Glu Lys Phe Lys Glu Ile
        195                 200                 205

Phe Leu Ile Ser Val Asn Thr Glu Ala Lys Leu Leu Tyr Asn Lys Asn
    210                 215                 220

Glu Gly Lys Asp Pro Ser Ile Phe Cys Asn Glu Leu Arg Asn Ser Phe
225                 230                 235                 240

Ser Asp Phe Arg Asn Ser Phe Ile Gly Asp Met Asp Phe Gly Gly
                245                 250                 255

Asn Thr Asp Arg Val Lys Gly Tyr Ile Asn Lys Lys Phe Ser Asp Tyr
            260                 265                 270

Tyr Lys Glu Lys Asn Val Glu Lys Leu Asn Asn Ile Lys Lys Glu Trp
        275                 280                 285

Trp Glu Lys Asn Lys Ala Asn Leu Trp Asn His Met Ile Val Asn His
    290                 295                 300

Lys Gly Asn Ile Ser Lys Glu Cys Ala Ile Ile Pro Ala Glu Glu Pro
305                 310                 315                 320

Gln Ile Asn Leu Trp Ile Lys Glu Trp Asn Glu Asn Phe Leu Met Glu
                325                 330                 335

Lys Lys Arg Leu Phe Leu Asn Ile Lys Asp Lys Cys Val Glu Asn Lys
            340                 345                 350

Lys Tyr Glu Ala Cys Phe Gly Gly Cys Arg Leu Pro Cys Ser Ser Tyr
```

-continued

```
              355                 360                 365
Thr Ser Phe Met Lys Lys Ser Lys Thr Gln Met Glu Val Leu Thr Asn
    370                 375                 380
Leu Tyr Lys Lys Lys Asn Ser Gly Val Asp Lys Asn Asn Phe Leu Asn
385                 390                 395                 400
Asp Leu Phe Lys Lys Asn Asn Lys Asn Asp Leu Asp Asp Phe Phe Lys
                405                 410                 415
Asn Glu Lys Glu Tyr Asp Asp Leu Cys Asp Cys Arg Tyr Thr Ala Thr
                420                 425                 430
Ile Ile Lys Ser Phe Leu Asn Gly Pro Ala Lys Asn Asp Val Asp Ile
            435                 440                 445
Ala Ser Gln Ile Asn Val Asn Asp Leu Arg Gly Phe Gly Cys Asn Tyr
    450                 455                 460
Lys Ser Asn Asn Glu Lys Ser Trp Asn Cys Thr Gly Thr Phe Thr Asn
465                 470                 475                 480
Lys Phe Pro Gly Thr Cys Glu Pro Pro Arg Arg Gln Thr Leu Cys Leu
                485                 490                 495
Gly Arg Thr Tyr Leu Leu His Arg Gly His Glu Glu Asp Tyr Lys Glu
                500                 505                 510
His Leu Leu Gly Ala Ser Ile Tyr Glu Ala Gln Leu Leu Lys Tyr Lys
            515                 520                 525
Tyr Lys Glu Lys Asp Glu Asn Ala Leu Cys Ser Ile Ile Gln Asn Ser
    530                 535                 540
Tyr Ala Asp Leu Ala Asp Ile Ile Lys Gly Ser Asp Ile Ile Lys Asp
545                 550                 555                 560
Tyr Tyr Gly Lys Lys Met Glu Glu Asn Leu Asn Lys Val Asn Lys Asp
                565                 570                 575
Lys Lys Arg Asn Glu Glu Ser Leu Lys Ile Phe Arg Glu Lys Trp Trp
                580                 585                 590
Asp Glu Asn Lys Glu Asn Val Trp Lys Val Met Ser Ala Val Leu Lys
                595                 600                 605
Asn Lys Glu Thr Cys Lys Asp Tyr Asp Lys Phe Gln Lys Ile Pro Gln
610                 615                 620
Phe Leu Arg Trp Phe Lys Glu Trp Gly Asp Asp Phe Cys Glu Lys Arg
625                 630                 635                 640
Lys Glu Lys Ile Tyr Ser Phe Glu Ser Phe Lys Val Glu Cys Lys Lys
                645                 650                 655
Lys Asp Cys Asp Glu Asn Thr Cys Lys Asn Lys Cys Ser Glu Tyr Lys
                660                 665                 670
Lys Trp Ile Asp Leu Lys Lys Ser Glu Tyr Glu Lys Gln Val Asp Lys
            675                 680                 685
Tyr Thr Lys Asp Lys Asn Lys Lys Met Tyr Asp Asn Ile Asp Glu Val
    690                 695                 700
Lys Asn Lys Glu Ala Asn Val Tyr Leu Lys Glu Ser Lys Glu Cys
705                 710                 715                 720
Lys Asp Val Asn Phe Asp Asp Lys Ile Phe Asn Glu Ser Pro Asn Glu
                725                 730                 735
Tyr Glu Asp Met Cys Lys Lys Cys Asp Glu Ile Lys Tyr Leu Asn Glu
                740                 745                 750
Ile Lys Tyr Pro Lys Thr Lys His Asp Ile Tyr Asp Ile Asp Thr Phe
            755                 760                 765
Ser Asp Thr Phe Gly Asp Gly Thr Pro Ile Ser Ile Asn Ala Asn Ile
    770                 775                 780
```

-continued

```
Asn Glu Gln Gln Ser Gly Lys Asp Thr Ser Asn Thr Gly Asn Ser Glu
785                 790                 795                 800

Thr Ser Asp Ser Pro Val Ser His Glu Pro Glu Ser Asp Ala Ala Ile
            805                 810                 815

Asn Val Glu Lys Leu Ser Gly Asp Glu Ser Ser Ser Glu Thr Arg Gly
        820                 825                 830

Ile Leu Asp Ile Asn Asp Pro Ser Val Thr Asn Val Asn Glu Val
    835                 840                 845

His Asp Ala Ser Asn Thr Gln Gly Ser Val Ser Asn Thr Ser Asp Ile
850                 855                 860

Thr Asn Gly His Ser Glu Ser Ser Leu Asn Arg Thr Thr Asn Ala Gln
865                 870                 875                 880

Asp Ile Lys Ile Gly Arg Ser Gly Asn Glu Gln Ser Asp Asn Gln Glu
                885                 890                 895

Asn Ser Ser His Ser Ser Asp Asn Ser Gly Ser Leu Thr Ile Gly Gln
            900                 905                 910

Val Pro Ser Glu Asp Asn Thr Gln Asn Thr Tyr Asp Ser Gln Asn Pro
        915                 920                 925

His Arg Asp Thr Pro Asn Ala Leu Ala Ser Leu Pro Ser Asp Asp Lys
    930                 935                 940

Ile Asn Glu Ile Glu Gly Phe Asp Ser Ser Arg Asp Ser Glu Asn Gly
945                 950                 955                 960

Arg Gly Asp Thr Thr Ser Asn Thr His Asp Val Arg Arg Thr Asn Ile
                965                 970                 975

Val Ser Glu Arg Arg Val Asn Ser His Asp Phe Ile Arg Asn Gly Met
            980                 985                 990

Ala Asn Asn Asn Ala His His Gln Tyr Ile Thr Gln Ile Glu Asn Asn
        995                 1000                1005

Gly Ile Ile Arg Gly Gln Glu Glu Ser Ala Gly Asn Ser Val Asn Tyr
    1010                1015                1020

Lys Asp Asn Pro Lys Arg Ser Asn Phe Ser Ser Glu Asn Asp His Lys
1025                1030                1035                1040

Lys Asn Ile Gln Glu Tyr Asn Ser Arg Asp Thr Lys Arg Val Arg Glu
                1045                1050                1055

Glu Ile Ile Lys Leu Ser Lys Gln Asn Lys Cys Asn Asn Glu Tyr Ser
            1060                1065                1070

Met Glu Tyr Cys Thr Tyr Ser Asp Glu Arg Asn Ser Ser Pro Gly Pro
        1075                1080                1085

Cys Ser Arg Glu Glu Arg Lys Lys Leu Cys Cys Gln Ile Ser Asp Tyr
    1090                1095                1100

Cys Leu Lys Tyr Phe Asn Phe Tyr Ser Ile Glu Tyr Tyr Asn Cys Ile
1105                1110                1115                1120

Lys Ser Glu Ile Lys Ser Pro Glu Tyr Lys Cys Phe Lys Ser Glu Gly
                1125                1130                1135

Gln Ser Ser Met Phe His Ile
            1140

<210> SEQ ID NO 2
<211> LENGTH: 1086
<212> TYPE: PRT
<213> ORGANISM: Plasmodium falciparum

<400> SEQUENCE: 2

Lys Cys Phe Phe Phe Leu Ser Lys Ser Ile Ile Arg Asn Lys Asp Val
```

```
  1               5                    10                   15
Asp Ile Ser Ile Lys Asp Phe Glu Lys Asn Lys Phe Ile Asp Thr Tyr
                20                  25                  30

Ser Leu Tyr Glu Cys Gly Lys Lys Ile Lys Glu Met Lys Trp Ile Cys
                35                  40                  45

Thr Asp Asn Gln Phe Lys Ser Asn Asn Leu Cys Ala Pro Ile Arg Arg
            50                  55                  60

Ile Gln Leu Cys Ile Val Asn Ile Ile Leu Phe Ser Glu Asn Glu Asn
 65                 70                  75                  80

Glu Tyr Ile Tyr Lys Asn Asp Ser Ile Asn Asn Lys Phe Lys Glu Asn
                85                  90                  95

Ile Leu Lys Ala Val Lys Leu Glu Ser Asn Leu Leu Val Gln Lys His
               100                 105                 110

Asn Asn Glu Tyr Asn Ser Lys Leu Cys Asp Asp Ile Arg Trp Ser Phe
               115                 120                 125

Leu Asp Tyr Gly Asp Ile Ile Ile Gly Arg Asp Leu Ile Tyr Lys Asn
           130                 135                 140

Asn Thr Asp Tyr Ile Lys Glu Gln Phe Lys Lys Ile Phe Asn Asn Glu
145                 150                 155                 160

Tyr Asn Asn Asn Glu Leu Asn Asp Glu Leu Asn Asn Glu Leu Asn Asp
                165                 170                 175

Glu Lys Asn Ile Lys Leu Arg Lys Glu Trp Trp Glu Lys Tyr Lys Glu
                180                 185                 190

Asp Ile Trp Glu Glu Met Thr Lys Glu His Asn Asp Lys Phe Ile Glu
           195                 200                 205

Lys Cys Lys Tyr Phe Ala Lys Asp Glu Pro Gln Ile Val Arg Trp Ile
   210                 215                 220

Glu Glu Trp Ser Lys Gln Phe Leu Asp Glu Lys Asn Tyr Met Leu Phe
225                 230                 235                 240

Thr Leu Arg Asn Thr Tyr Asn Glu Met Asn Ile Ile His Glu Asn Asn
                245                 250                 255

Cys Lys Gln Tyr Asn Lys Trp Val Gln Asn Arg Lys Lys Glu Trp Thr
                260                 265                 270

Phe Leu Ser Asn Glu Phe Asn Lys Ile Phe Pro Glu Arg Asn Val Gln
   275                 280                 285

Ile His Ile Ser Asn Ile Phe Lys Glu Tyr Lys Glu Asn Asn Val Asp
   290                 295                 300

Ile Ile Phe Gly Thr Leu Asn Tyr Glu Tyr Asn Asn Phe Cys Lys Glu
305                 310                 315                 320

Lys Pro Glu Leu Val Ser Ala Ala Lys Tyr Asn Leu Lys Ala Pro Asn
                325                 330                 335

Ala Lys Ser Pro Arg Ile Tyr Lys Ser Lys Glu His Glu Glu Ser Ser
           340                 345                 350

Val Phe Gly Cys Lys Thr Lys Ile Ser Lys Val Lys Lys Lys Trp Asn
           355                 360                 365

Cys Tyr Ser Asn Asn Lys Val Thr Lys Pro Glu Gly Val Cys Gly Pro
   370                 375                 380

Pro Arg Arg Gln Gln Leu Cys Leu Gly Tyr Ile Phe Leu Ile Arg Asp
385                 390                 395                 400

Gly Asn Glu Glu Gly Leu Lys Asp His Ile Asn Lys Ala Ala Asn Tyr
                405                 410                 415

Glu Ala Met His Leu Lys Glu Lys Tyr Glu Asn Ala Gly Gly Asp Lys
           420                 425                 430
```

-continued

```
Ile Cys Asn Ala Ile Leu Gly Ser Tyr Ala Asp Ile Gly Asp Ile Val
        435                 440                 445

Arg Gly Leu Asp Val Trp Arg Asp Ile Asn Thr Asn Lys Leu Ser Glu
    450                 455                 460

Lys Phe Gln Lys Ile Phe Met Gly Gly Asn Ser Arg Lys Lys Gln
465                 470                 475                 480

Asn Asp Asn Asn Glu Arg Asn Lys Trp Trp Glu Lys Gln Arg Asn Leu
                485                 490                 495

Ile Trp Ser Ser Met Val Lys His Ile Pro Lys Gly Lys Thr Cys Lys
            500                 505                 510

Arg His Asn Asn Phe Glu Lys Ile Pro Gln Phe Leu Arg Trp Leu Lys
        515                 520                 525

Glu Trp Gly Asp Glu Phe Cys Glu Glu Met Gly Thr Glu Val Lys Gln
    530                 535                 540

Leu Glu Lys Ile Cys Glu Asn Lys Asn Cys Ser Glu Lys Lys Cys Lys
545                 550                 555                 560

Asn Ala Cys Ser Ser Tyr Glu Lys Trp Ile Lys Glu Arg Lys Asn Glu
                565                 570                 575

Tyr Asn Leu Gln Ser Lys Lys Phe Asp Ser Asp Lys Lys Leu Asn Lys
            580                 585                 590

Lys Asn Asn Leu Tyr Asn Lys Phe Glu Asp Ser Lys Ala Tyr Leu Arg
        595                 600                 605

Ser Glu Ser Lys Gln Cys Ser Asn Ile Glu Phe Asn Asp Glu Thr Phe
    610                 615                 620

Thr Phe Pro Asn Lys Tyr Lys Glu Ala Cys Met Val Cys Glu Asn Pro
625                 630                 635                 640

Ser Ser Ser Lys Ala Leu Lys Pro Ile Lys Thr Asn Val Phe Pro Ile
                645                 650                 655

Glu Glu Ser Lys Lys Ser Glu Leu Ser Ser Leu Thr Asp Lys Ser Lys
            660                 665                 670

Asn Thr Pro Asn Ser Ser Gly Gly Gly Asn Tyr Gly Asp Arg Gln Ile
        675                 680                 685

Ser Lys Arg Asp Asp Val His His Asp Gly Pro Lys Glu Val Lys Ser
    690                 695                 700

Gly Glu Lys Glu Val Pro Lys Ile Asp Ala Ala Val Lys Thr Glu Asn
705                 710                 715                 720

Glu Phe Thr Ser Asn Arg Asn Asp Ile Glu Gly Lys Glu Lys Ser Lys
                725                 730                 735

Gly Asp His Ser Ser Pro Val His Ser Lys Asp Ile Lys Asn Glu Glu
            740                 745                 750

Pro Gln Arg Val Val Ser Glu Asn Leu Pro Lys Ile Glu Glu Lys Met
        755                 760                 765

Glu Ser Ser Asp Ser Ile Pro Ile Thr His Ile Glu Ala Glu Lys Gly
    770                 775                 780

Gln Ser Ser Asn Ser Ser Asp Asn Asp Pro Ala Val Val Ser Gly Arg
785                 790                 795                 800

Glu Ser Lys Asp Val Asn Leu His Thr Ser Glu Arg Ile Lys Glu Asn
                805                 810                 815

Glu Glu Gly Val Ile Lys Thr Asp Glu Ser Ser Lys Ser Ile Glu Ile
            820                 825                 830

Ser Lys Ile Pro Ser Asp Gln Asn Asn His Ser Asp Leu Ser Gln Asn
        835                 840                 845
```

```
Ala Asn Glu Asp Ser Asn Gln Gly Asn Lys Glu Thr Ile Asn Pro Pro
    850                 855                 860

Ser Thr Glu Lys Asn Leu Lys Glu Ile His Tyr Lys Thr Ser Asp Ser
865                 870                 875                 880

Asp Asp His Gly Ser Lys Ile Lys Ser Glu Ile Glu Pro Lys Glu Leu
                885                 890                 895

Thr Glu Glu Ser Pro Leu Thr Asp Lys Lys Thr Glu Ser Ala Ala Ile
            900                 905                 910

Gly Asp Lys Asn His Glu Ser Val Lys Ser Ala Asp Ile Phe Gln Ser
        915                 920                 925

Glu Ile His Asn Ser Asp Asn Arg Asp Arg Ile Val Ser Glu Ser Val
    930                 935                 940

Val Gln Asp Ser Ser Gly Ser Ser Met Ser Thr Glu Ser Ile Arg Thr
945                 950                 955                 960

Asp Asn Lys Asp Phe Lys Thr Ser Glu Asp Ile Ala Pro Ser Ile Asn
                965                 970                 975

Gly His Glu Lys Ile Gly Ser Ser Ala Asp Arg Gly Ser Glu Asp
            980                 985                 990

Lys Ser Ile Ile Asp Lys Asp Ser Glu Asn Phe Glu Asn Asn Lys Ser
        995                 1000                1005

Ser His Ser Asp Ile Lys Gln Ser Asp Asn Glu Gly Ser Thr Asp Tyr
    1010                1015                1020

Glu Ser Leu Thr Glu Glu Ser Pro Lys Gly Asp Leu Glu Ser Val Ser
1025                1030                1035                1040

Pro Ser Ser Ile Asp Met Asp Leu Lys Pro Asn Lys Ser Ser Pro Val
                1045                1050                1055

Thr Ser Phe Asp His Val Asp Ser Pro Asn Ile Ser Glu Leu Gln Ser
            1060                1065                1070

Ala Ser Gln Asn Ala Asp Ser Tyr Gln Gly Glu Lys Pro Ser
        1075                1080                1085

<210> SEQ ID NO 3
<211> LENGTH: 972
<212> TYPE: PRT
<213> ORGANISM: Plasmodium falciparum

<400> SEQUENCE: 3

Trp Asn Gly Leu Met Ile Gln Ile Ile Lys Ile Tyr Gly Ile Ile
1               5                   10                  15

Asn Trp Met Ile Leu Lys Ile Asn Val Ile Glu Phe Val Gln Lys Lys
            20                  25                  30

Glu Ile Cys Lys Ser Glu Cys Lys Lys Tyr Lys Ala Trp Ile Asp Lys
        35                  40                  45

Lys Asn Asn Asp Phe Thr Ile Leu Ser Glu Ile Tyr Leu Lys Tyr Asn
    50                  55                  60

Lys Lys Ser Ser Leu Tyr Lys Thr Ala Phe Glu Tyr Leu Lys Gln Lys
65                  70                  75                  80

Trp Asp Lys Tyr Lys Glu Leu Asn Phe Ser Ser Ile Phe Asp Gln Leu
                85                  90                  95

Asn Ala Lys Tyr Tyr Asn Lys Cys Ile Cys Gln Asn Asn Lys Ile Glu
            100                 105                 110

Asn Asn Ala Leu Tyr Val Lys Ile Glu Asp Ile Cys Asn Asn Thr Lys
        115                 120                 125

Val Lys Ser Ile Tyr Gly Glu Leu Tyr Cys Lys Glu Lys Gly Asn Asp
    130                 135                 140
```

```
Lys Ile Trp Gln Cys Ile Asn Glu His Ile Lys Asp Phe Pro Asp Val
145                 150                 155                 160

Cys Gly Pro Pro Arg Arg Gln Gln Leu Cys Leu Gly Asn Leu Asp Lys
            165                 170                 175

Asp Glu Phe Lys Asn Val Asn Asp Leu Lys Lys Phe Leu Asn Glu Ile
            180                 185                 190

Ile Leu Gly Ile Arg Asp Glu Gly Lys Phe Leu Ile Glu Lys Tyr Arg
        195                 200                 205

Lys Asn Met His Glu Asn Met Tyr Leu Asp Glu Arg Ala Cys Lys Tyr
        210                 215                 220

Leu Asn Tyr Ser Phe Asp Asp Tyr Lys Asn Ile Ile Leu Gly Lys Asp
225                 230                 235                 240

Met Trp Arg Asp Pro Asn Ser Ile Lys Thr Glu Asn Ile Leu Lys Gly
                245                 250                 255

Asn Phe Glu Gly Ile Lys Ala Asn Ile Val Ser Met Tyr Pro Ser Tyr
            260                 265                 270

Ala Asp Leu Ser Leu Asp Glu Phe Arg Lys His Trp Trp Asp Gln Asn
            275                 280                 285

Lys Lys Gln Leu Trp Glu Ala Ile Ser Cys Glu Phe Tyr Lys Gly Asn
290                 295                 300

His Thr Gly Val Cys Leu Met Glu Asp Asn Asp Asn Gln Tyr Leu
305                 310                 315                 320

His Trp Phe Arg Glu Trp Lys Asn Asp Phe Cys Ile Asp Lys Leu Lys
                325                 330                 335

Trp Asn Asp Val Ile Lys Glu Pro Cys Ile Asp Lys Lys Val Lys Ser
            340                 345                 350

Pro Lys Pro Ser Glu Asn Pro Ser Asp Val Ala Thr Val Cys Asn Lys
            355                 360                 365

Ser Cys Thr Asp Tyr Asp Lys Trp Ile Ile Asn Lys Arg Lys Glu Tyr
    370                 375                 380

Lys Met Gln Ser Ser Lys Tyr Lys Arg Asp Arg Ser Leu Phe Asn Asn
385                 390                 395                 400

Val Ile Gln Asn Leu Lys Pro Trp Glu Tyr Leu Ser Met Lys Cys Thr
            405                 410                 415

Glu Cys Thr Cys Asn Leu Asp Thr Gln Thr Phe Val Tyr Pro Tyr Lys
            420                 425                 430

Gly Tyr Glu Asp Ile Cys Lys Ser Thr Val Lys Pro Tyr Asp Pro Glu
        435                 440                 445

Asp Ile Lys Asp Glu Glu Phe Asn Glu Pro Ser Leu Asn Val Asn Pro
450                 455                 460

Leu Ser Leu Thr Ser Gln Asp Val Thr Glu Arg Val Ser Ser Val Asp
465                 470                 475                 480

Asp Val Leu Ser Ile Lys Glu Asn Val Asp Leu Lys Pro Phe Lys Pro
            485                 490                 495

Lys Gly Gly Thr Gln Ser Ser His Val Asp Gln Val Gly Asn Pro Arg
            500                 505                 510

Glu Ser Glu Ser Lys Pro Ser Gly Ala Asn Gly Arg Glu Asp Pro Ser
            515                 520                 525

Thr Glu Ser Ser Thr Tyr Asn Asp Gly Val Ile Thr Ser Ser Ser
            530                 535                 540

Leu Gly Ser Ser Ser Gly Arg Asp Val Ser Ser Ser Pro Val Gly Val
545                 550                 555                 560
```

-continued

```
Gly Asp Glu His Glu Ala Lys Glu Leu Leu Pro Pro Gln Lys Ile Ile
            565                 570                 575

Asp Gly Val Thr Gln Ser Asp Glu Ser Thr Leu Ser Gln His Gly Lys
            580                 585                 590

Glu Ser Ser Gln Glu Gln His Asn Leu Asp Gly Ser Ser Leu Ser Arg
            595                 600                 605

His Ser Asn Gln Asp Glu Glu Arg Ser Ile Ile Thr Ser Asp Val Glu
            610                 615                 620

His Gly Thr Asn Ser Leu Phe Gly Ser Gln Ile Gln Asp Gln Glu Thr
625                 630                 635                 640

Ile Leu Gly Glu Ser Glu Pro Leu Thr Thr Ser Pro Pro Glu His Glu
                645                 650                 655

Thr Ser Lys Met Asp Thr His Ala Gly Gly Lys Asn Met Glu Gln Val
                660                 665                 670

Arg Asn Ala Ser Val Asp Ser Ser Glu Met Ser Asn Gly Gly Arg
            675                 680                 685

Gly Gly Leu Lys Thr Lys Glu Met Lys Gly Glu Val Thr Gly Ile
            690                 695                 700

Thr Ser Lys Asn Asp Ile Asn Leu Glu Asp Ser Thr Val His Ser Arg
705                 710                 715                 720

Gln Asn Lys Ile Glu Asn Ser Gly Asp Asn Thr Gln Gly Lys Glu His
                725                 730                 735

Ile Asn Val Leu Gln Gly Met Asp Lys His Leu Glu Asn Pro Pro Thr
                740                 745                 750

Ser Glu Arg Gly Asp Ser Val Leu Glu Ser Glu Phe Ser Lys Leu Asn
            755                 760                 765

Arg Thr Ser His Thr His Asp Asn Asn Arg Ile Glu Thr Thr Ala Glu
            770                 775                 780

Asn Asn Ile Gly Gly Leu Ser Asn Ser Asn Val His Asp Gly Arg Asp
785                 790                 795                 800

Ser Gln Arg Asn Arg Met His Ile Asn Ser Arg Ser Arg His Gly Ser
                805                 810                 815

Leu Glu Ser Asp Ile Val Val Arg Gly Asp Ile Ser Asn Ile Glu
            820                 825                 830

Gly Gly Glu Glu Glu Glu Asp Ala Asn Thr Leu Lys Tyr Pro Arg
            835                 840                 845

Asn Val Leu Asn Asn Lys Asn Ser Arg Thr Tyr Asn Ile Glu Glu Tyr
            850                 855                 860

Ile Tyr Arg Asp Val Asn Lys Val Ala Asp Asp Ile Met Arg Ser Tyr
865                 870                 875                 880

Lys Ser Asn Arg Cys Thr Asn Asn Leu Ser Ser Asn Tyr Cys Ser Lys
                885                 890                 895

Leu Lys Lys Glu Ser Leu Ser Asn Thr Cys Thr Asn Glu Asp Ser Lys
            900                 905                 910

Arg Leu Cys Cys Ser Ile Ser Asp Tyr Cys Met Lys Phe Phe Asn Phe
            915                 920                 925

Asn Ser Ser Gly Tyr His Ser Cys Met Arg Lys Glu Phe Ser Asn His
            930                 935                 940

Ala Tyr Lys Cys Phe Ala Gly Lys Gly Phe Ser Ser Met Phe Asn Leu
945                 950                 955                 960

Asp Lys Lys Lys Lys Lys Lys Lys Lys Gly
                965                 970
```

<210> SEQ ID NO 4
<211> LENGTH: 1501
<212> TYPE: PRT
<213> ORGANISM: Plasmodium falciparum

<400> SEQUENCE: 4

```
Asn Asn Met Lys Gly Lys Met Asn Met Cys Leu Phe Phe Tyr Ser
 1               5                  10                  15

Ile Leu Tyr Val Val Leu Cys Thr Tyr Val Leu Gly Ile Ser Glu Glu
            20                  25                  30

Tyr Leu Lys Glu Arg Pro Gln Gly Leu Asn Val Glu Thr Asn Asn Asn
        35                  40                  45

Asn Asn Asn Asn Asn Asn Asn Ser Asn Ser Asn Asp Ala Met Ser
50                  55                  60

Phe Val Asn Glu Val Ile Arg Phe Ile Glu Asn Glu Lys Asp Asp Lys
65                  70                  75                  80

Glu Asp Lys Lys Val Lys Ile Ile Ser Arg Pro Val Glu Asn Thr Leu
                85                  90                  95

His Arg Tyr Pro Val Ser Ser Phe Leu Asn Ile Lys Lys Tyr Gly Arg
            100                 105                 110

Lys Gly Glu Tyr Leu Asn Arg Asn Ser Phe Val Gln Arg Ser Tyr Ile
        115                 120                 125

Arg Gly Cys Lys Gly Lys Arg Ser Thr His Thr Trp Ile Cys Glu Asn
130                 135                 140

Lys Gly Asn Asn Asn Ile Cys Ile Pro Asp Arg Arg Val Gln Leu Cys
145                 150                 155                 160

Ile Thr Ala Leu Gln Asp Leu Lys Asn Ser Gly Ser Glu Thr Thr Asp
                165                 170                 175

Arg Lys Leu Leu Arg Asp Lys Val Phe Asp Ser Ala Met Tyr Glu Thr
            180                 185                 190

Asp Leu Leu Trp Asn Lys Tyr Gly Phe Arg Gly Phe Asp Asp Phe Cys
        195                 200                 205

Asp Asp Val Lys Asn Ser Tyr Leu Asp Tyr Lys Asp Val Ile Phe Gly
    210                 215                 220

Thr Asp Leu Asp Lys Asn Asn Ile Ser Lys Leu Val Glu Glu Ser Leu
225                 230                 235                 240

Lys Arg Phe Phe Lys Lys Asp Ser Ser Val Leu Asn Pro Thr Ala Trp
                245                 250                 255

Trp Arg Arg Tyr Gly Thr Arg Leu Trp Lys Thr Met Ile Gln Pro Tyr
            260                 265                 270

Ala His Leu Gly Cys Arg Lys Pro Asp Glu Asn Glu Pro Gln Ile Asn
        275                 280                 285

Arg Trp Ile Leu Glu Trp Gly Lys Tyr Asn Cys Arg Leu Met Lys Glu
    290                 295                 300

Lys Glu Lys Leu Leu Thr Gly Glu Cys Ser Val Asn Arg Lys Lys Ser
305                 310                 315                 320

Asp Cys Ser Thr Gly Cys Asn Asn Glu Cys Tyr Thr Tyr Arg Ser Leu
                325                 330                 335

Ile Asn Arg Gln Arg Tyr Glu Val Ser Ile Leu Gly Lys Lys Tyr Ile
            340                 345                 350

Lys Val Val Arg Tyr Thr Ile Phe Arg Arg Lys Ile Val Gln Pro Asp
        355                 360                 365

Asn Ala Leu Asp Phe Leu Lys Leu Asn Cys Ser Glu Cys Lys Asp Ile
    370                 375                 380
```

-continued

```
Asp Phe Lys Pro Phe Phe Glu Phe Glu Tyr Gly Lys Tyr Glu Glu Lys
385                 390                 395                 400

Cys Met Cys Gln Ser Tyr Ile Asp Leu Lys Ile Gln Phe Lys Asn Asn
            405                 410                 415

Asp Ile Cys Ser Phe Asn Ala Gln Thr Asp Thr Val Ser Ser Asp Lys
        420                 425                 430

Arg Phe Cys Leu Glu Lys Lys Glu Phe Lys Pro Trp Lys Cys Asp Lys
    435                 440                 445

Asn Ser Phe Glu Thr Val His His Lys Gly Val Cys Val Ser Pro Arg
450                 455                 460

Arg Gln Gly Phe Cys Leu Gly Asn Leu Asn Tyr Leu Leu Asn Asp Asp
465                 470                 475                 480

Ile Tyr Asn Val His Asn Ser Gln Leu Leu Ile Glu Ile Met Ala
                485                 490                 495

Ser Lys Gln Glu Gly Lys Leu Leu Trp Lys Lys His Gly Thr Ile Leu
            500                 505                 510

Asp Asn Gln Asn Ala Cys Lys Tyr Ile Asn Asp Ser Tyr Val Asp Tyr
        515                 520                 525

Lys Asp Ile Val Ile Gly Asn Asp Leu Trp Asn Asp Asn Ser Ile
530                 535                 540

Lys Val Gln Asn Asn Leu Asn Leu Ile Phe Glu Arg Asn Phe Gly Tyr
545                 550                 555                 560

Lys Val Gly Arg Asn Lys Leu Phe Lys Thr Ile Lys Glu Leu Lys Asn
                565                 570                 575

Val Trp Trp Ile Leu Asn Arg Asn Lys Val Trp Glu Ser Met Arg Cys
            580                 585                 590

Gly Ile Asp Glu Val Asp Gln Arg Arg Lys Thr Cys Glu Arg Ile Asp
        595                 600                 605

Glu Leu Glu Asn Met Pro Gln Phe Phe Arg Trp Phe Ser Gln Trp Ala
610                 615                 620

His Phe Phe Cys Lys Glu Lys Glu Tyr Trp Glu Leu Lys Leu Asn Asp
625                 630                 635                 640

Lys Cys Thr Gly Asn Asn Gly Lys Ser Leu Cys Gln Asp Lys Thr Cys
                645                 650                 655

Gln Asn Val Cys Thr Asn Met Asn Tyr Trp Thr Tyr Thr Arg Lys Leu
            660                 665                 670

Ala Tyr Glu Ile Gln Ser Val Lys Tyr Asp Lys Asp Arg Lys Leu Phe
        675                 680                 685

Ser Leu Ala Lys Asp Lys Asn Val Thr Thr Phe Leu Lys Glu Asn Ala
690                 695                 700

Lys Asn Cys Ser Asn Ile Asp Phe Thr Lys Ile Phe Asp Gln Leu Asp
705                 710                 715                 720

Lys Leu Phe Lys Glu Arg Cys Ser Cys Met Asp Thr Gln Val Leu Glu
                725                 730                 735

Val Lys Asn Lys Glu Met Leu Ser Ile Asp Ser Asn Ser Glu Asp Ala
            740                 745                 750

Thr Asp Ile Ser Glu Lys Asn Gly Glu Glu Leu Tyr Val Asn His
        755                 760                 765

Asn Ser Val Ser Val Ala Ser Gly Asn Lys Glu Ile Glu Lys Ser Lys
770                 775                 780

Asp Glu Lys Gln Pro Glu Lys Glu Ala Lys Gln Thr Asn Gly Thr Leu
785                 790                 795                 800

Thr Val Arg Thr Asp Lys Asp Ser Asp Arg Asn Lys Gly Lys Asp Thr
```

-continued

```
                805                 810                 815
Ala Thr Asp Thr Lys Asn Ser Pro Glu Asn Leu Lys Val Gln Glu His
            820                 825                 830
Gly Thr Asn Gly Glu Thr Ile Lys Glu Pro Pro Lys Leu Pro Glu
        835                 840                 845
Ser Ser Glu Thr Leu Gln Ser Gln Gln Leu Glu Ala Glu Ala Gln
    850                 855                 860
Lys Gln Lys Gln Glu Glu Glu Pro Lys Lys Gln Glu Glu Glu Pro
865                 870                 875                 880
Lys Lys Lys Gln Glu Glu Gln Lys Arg Glu Gln Glu Gln Lys Gln
                885                 890                 895
Glu Gln Glu Glu Glu Gln Lys Gln Glu Glu Gln Gln Ile Gln
            900                 905                 910
Asp Gln Ser Gln Ser Gly Leu Asp Gln Ser Ser Lys Val Gly Val Ala
        915                 920                 925
Ser Glu Gln Asn Glu Ile Ser Ser Gly Gln Glu Gln Asn Val Lys Ser
    930                 935                 940
Ser Ser Pro Glu Val Val Pro Gln Glu Thr Thr Ser Glu Asn Gly Ser
945                 950                 955                 960
Ser Gln Asp Thr Lys Ile Ser Ser Thr Glu Pro Asn Glu Asn Ser Val
                965                 970                 975
Val Asp Arg Ala Thr Asp Ser Met Asn Leu Asp Pro Glu Lys Val His
            980                 985                 990
Asn Glu Asn Met Ser Asp Pro Asn Thr Asn Thr Glu Pro Asp Ala Ser
        995                 1000                1005
Leu Lys Asp Asp Lys Lys Glu Val Asp Ala Lys Lys Glu Leu Gln
    1010                1015                1020
Ser Thr Val Ser Arg Ile Glu Ser Asn Glu Gln Asp Val Gln Ser Thr
1025                1030                1035                1040
Pro Pro Glu Asp Thr Pro Thr Val Glu Gly Lys Val Gly Asp Lys Ala
                1045                1050                1055
Glu Met Leu Thr Ser Pro His Ala Thr Asp Asn Ser Glu Ser Glu Ser
            1060                1065                1070
Gly Leu Asn Pro Thr Asp Asp Ile Lys Thr Thr Asp Gly Val Val Lys
        1075                1080                1085
Glu Gln Glu Ile Leu Gly Gly Glu Ser Ala Thr Glu Thr Ser Lys
    1090                1095                1100
Ser Asn Leu Glu Lys Pro Lys Asp Val Glu Pro Ser His Glu Ile Ser
1105                1110                1115                1120
Glu Pro Val Leu Ser Gly Thr Thr Gly Lys Glu Glu Ser Glu Leu Leu
                1125                1130                1135
Lys Ser Lys Ser Ile Glu Thr Lys Gly Glu Thr Asp Pro Arg Ser Asn
            1140                1145                1150
Asp Gln Glu Asp Ala Thr Asp Val Val Glu Asn Ser Arg Asp Asp
        1155                1160                1165
Asn Asn Ser Leu Ser Asn Ser Val Asp Asn Gln Ser Asn Val Leu Asn
    1170                1175                1180
Arg Glu Asp Pro Ile Ala Ser Glu Thr Glu Val Val Ser Glu Pro Glu
1185                1190                1195                1200
Asp Ser Ser Arg Ile Ile Thr Thr Glu Val Pro Ser Thr Thr Val Lys
                1205                1210                1215
Pro Pro Asp Glu Lys Arg Ser Glu Glu Val Gly Glu Lys Glu Ala Lys
            1220                1225                1230
```

```
Glu Ile Lys Val Glu Pro Val Val Pro Arg Ala Ile Gly Glu Pro Met
            1235                1240                1245

Glu Asn Ser Val Ser Val Gln Ser Pro Pro Asn Val Glu Asp Val Glu
        1250                1255                1260

Lys Glu Thr Leu Ile Ser Glu Asn Asn Gly Leu His Asn Asp Thr His
1265                1270                1275                1280

Arg Gly Asn Ile Ser Glu Lys Asp Leu Ile Asp Ile His Leu Leu Arg
                1285                1290                1295

Asn Glu Ala Gly Ser Thr Ile Leu Asp Asp Ser Arg Arg Asn Gly Glu
            1300                1305                1310

Met Thr Glu Gly Ser Glu Ser Asp Val Gly Glu Leu Gln Glu His Asn
        1315                1320                1325

Phe Ser Thr Gln Gln Lys Asp Glu Lys Asp Phe Asp Gln Ile Ala Ser
        1330                1335                1340

Asp Arg Glu Lys Glu Glu Ile Gln Lys Leu Leu Asn Ile Gly His Glu
1345                1350                1355                1360

Glu Asp Glu Asp Val Leu Lys Met Asp Arg Thr Glu Asp Ser Met Ser
                1365                1370                1375

Asp Gly Val Asn Ser His Leu Tyr Tyr Asn Asn Leu Ser Ser Glu Glu
            1380                1385                1390

Lys Met Glu Gln Tyr Asn Asn Arg Asp Ala Ser Lys Asp Arg Glu Glu
        1395                1400                1405

Ile Leu Asn Arg Ser Asn Thr Asn Thr Cys Ser Asn Glu His Ser Leu
1410                1415                1420

Lys Tyr Cys Gln Tyr Met Glu Arg Asn Lys Asp Leu Leu Glu Thr Cys
1425                1430                1435                1440

Ser Glu Asp Lys Arg Leu His Leu Cys Cys Glu Ile Ser Asp Tyr Cys
                1445                1450                1455

Leu Lys Phe Phe Asn Pro Lys Ser Ile Glu Tyr Phe Asp Cys Thr Gln
            1460                1465                1470

Lys Glu Phe Asp Asp Pro Thr Tyr Asn Cys Phe Arg Lys Gln Arg Phe
        1475                1480                1485

Thr Ser Met Ser Cys Tyr Lys Ile Lys Asn Asn Ile His
        1490                1495                1500

<210> SEQ ID NO 5
<211> LENGTH: 4
<212> TYPE: PRT
<213> ORGANISM: Artificial Sequence
<220> FEATURE:
<223> OTHER INFORMATION: synthetic peptide

<400> SEQUENCE: 5

Gly Gly Gly Ser
 1

<210> SEQ ID NO 6
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 6
caaggagaat gtatggaaag ta                                          22

<210> SEQ ID NO 7
```

```
<211> LENGTH: 23
<212> TYPE: DNA
<213> ORGANISM: Artificial Sequence
<220> FEATURE:
<223> OTHER INFORMATION: synthetic oligonucleotide reverse primer

<400> SEQUENCE: 7
atcttcatat tcatttggac tct                                            23

<210> SEQ ID NO 8
<211> LENGTH: 38
<212> TYPE: DNA
<213> ORGANISM: Artificial Sequence
<220> FEATURE:
<223> OTHER INFORMATION: EBP2 forward primer

<400> SEQUENCE: 8
atgcggatcc caatatacgt ttatacagaa acgtactc                            38

<210> SEQ ID NO 9
<211> LENGTH: 34
<212> TYPE: DNA
<213> ORGANISM: Artificial Sequence
<220> FEATURE:
<223> OTHER INFORMATION: EBP2 reverse primer

<400> SEQUENCE: 9
atgcggatcc tcatatatcg tgttttgttt tagg                                34

<210> SEQ ID NO 10
<211> LENGTH: 24
<212> TYPE: DNA
<213> ORGANISM: Artificial Sequence
<220> FEATURE:
<223> OTHER INFORMATION: EBP2 forward primer

<400> SEQUENCE: 10
tctagagata ctaaaagagt aagg                                           24

<210> SEQ ID NO 11
<211> LENGTH: 23
<212> TYPE: DNA
<213> ORGANISM: Artificial Sequence
<220> FEATURE:
<223> OTHER INFORMATION: EBP2 reverse primer

<400> SEQUENCE: 11
tgattgaccc tcgcttttaa aac                                            23

<210> SEQ ID NO 12
<211> LENGTH: 34
<212> TYPE: DNA
<213> ORGANISM: Artificial Sequence
<220> FEATURE:
<223> OTHER INFORMATION: EBP3 forward primer

<400> SEQUENCE: 12
atgcggatcc gaaaagaata aatttattga cact                                34

<210> SEQ ID NO 13
<211> LENGTH: 37
<212> TYPE: DNA
<213> ORGANISM: Artificial Sequence
<220> FEATURE:
<223> OTHER INFORMATION: EBP3 reverse primer

<400> SEQUENCE: 13
```

```
atgcggatcc tcaaggaaac acattcgttt ttatagg                          37
```

<210> SEQ ID NO 14
<211> LENGTH: 37
<212> TYPE: DNA
<213> ORGANISM: Artificial Sequence
<220> FEATURE:
<223> OTHER INFORMATION: EBP4 forward primer

<400> SEQUENCE: 14

```
atgcggatcc aatctgaaag ctccaaatgc taaatcc                          37
```

<210> SEQ ID NO 15
<211> LENGTH: 40
<212> TYPE: DNA
<213> ORGANISM: Artificial Sequence
<220> FEATURE:
<223> OTHER INFORMATION: EBP4 reverse primer

<400> SEQUENCE: 15

```
atgcggatcc tcatatagga aacacattcg tttttatagg                       40
```

<210> SEQ ID NO 16
<211> LENGTH: 31
<212> TYPE: DNA
<213> ORGANISM: Artificial Sequence
<220> FEATURE:
<223> OTHER INFORMATION: EBP5 forward primer

<400> SEQUENCE: 16

```
atgcggatcc aatagaaata gttttgttca a                                31
```

<210> SEQ ID NO 17
<211> LENGTH: 34
<212> TYPE: DNA
<213> ORGANISM: Artificial Sequence
<220> FEATURE:
<223> OTHER INFORMATION: EBP5 reverse primer

<400> SEQUENCE: 17

```
atgcggatcc tcatgagtct atagataaca tttc                             34
```

<210> SEQ ID NO 18
<211> LENGTH: 1421
<212> TYPE: PRT
<213> ORGANISM: Plasmodium falciparum

<400> SEQUENCE: 18

```
Met Lys Cys Asn Ile Ser Ile Tyr Phe Phe Ala Ser Phe Phe Val Leu
  1               5                  10                  15

Tyr Phe Ala Lys Ala Arg Asn Glu Tyr Asp Ile Lys Glu Asn Glu Lys
                 20                  25                  30

Phe Leu Asp Val Tyr Lys Glu Lys Phe Asn Glu Leu Asp Lys Lys Lys
             35                  40                  45

Tyr Gly Asn Val Gln Lys Thr Asp Lys Lys Ile Phe Thr Phe Ile Glu
         50                  55                  60

Asn Lys Leu Asp Ile Leu Asn Asn Ser Lys Phe Asn Lys Arg Trp Lys
 65                  70                  75                  80

Ser Tyr Gly Thr Pro Asp Asn Ile Asp Lys Asn Met Ser Leu Ile Asn
                 85                  90                  95

Lys His Asn Asn Glu Glu Met Phe Asn Asn Asn Tyr Gln Ser Phe Leu
                100                 105                 110
```

```
Ser Thr Ser Ser Leu Ile Lys Gln Asn Lys Tyr Val Pro Ile Asn Ala
        115                 120                 125
Val Arg Val Ser Arg Ile Leu Ser Phe Leu Asp Ser Arg Ile Asn Asn
    130                 135                 140
Gly Arg Asn Thr Ser Ser Asn Asn Glu Val Leu Ser Asn Cys Arg Glu
145                 150                 155                 160
Lys Arg Lys Gly Met Lys Trp Asp Cys Lys Lys Asn Asp Arg Ser
                165                 170                 175
Asn Tyr Val Cys Ile Pro Asp Arg Arg Ile Gln Leu Cys Ile Val Asn
            180                 185                 190
Leu Ser Ile Ile Lys Thr Tyr Thr Lys Glu Thr Met Lys Asp His Phe
        195                 200                 205
Ile Glu Ala Ser Lys Lys Glu Ser Gln Leu Leu Lys Lys Asn Asp
    210                 215                 220
Asn Lys Tyr Asn Ser Lys Phe Cys Asn Asp Leu Lys Asn Ser Phe Leu
225                 230                 235                 240
Asp Tyr Gly His Leu Ala Met Gly Asn Asp Met Asp Phe Gly Gly Tyr
            245                 250                 255
Ser Thr Lys Ala Glu Asn Lys Ile Gln Glu Val Phe Lys Gly Ala His
        260                 265                 270
Gly Glu Ile Ser Glu His Lys Ile Lys Asn Phe Arg Lys Lys Trp Trp
        275                 280                 285
Asn Glu Phe Arg Glu Lys Leu Trp Glu Ala Met Leu Ser Glu His Lys
    290                 295                 300
Asn Asn Ile Asn Asn Cys Lys Asn Ile Pro Gln Glu Glu Leu Gln Ile
305                 310                 315                 320
Thr Gln Trp Ile Lys Glu Trp His Gly Glu Phe Leu Leu Glu Arg Asp
                325                 330                 335
Asn Arg Ser Lys Leu Pro Lys Ser Lys Cys Lys Asn Asn Thr Leu Tyr
            340                 345                 350
Glu Ala Cys Glu Lys Glu Cys Ile Asp Pro Cys Met Lys Tyr Arg Asp
            355                 360                 365
Trp Ile Ile Arg Ser Lys Phe Glu Trp His Thr Leu Ser Lys Glu Tyr
        370                 375                 380
Glu Thr Gln Lys Val Pro Lys Glu Asn Ala Glu Asn Tyr Leu Ile Lys
385                 390                 395                 400
Ile Ser Glu Asn Lys Asn Asp Ala Lys Val Ser Leu Leu Leu Asn Asn
            405                 410                 415
Cys Asp Ala Glu Tyr Ser Lys Tyr Cys Asp Cys Lys His Thr Thr Thr
            420                 425                 430
Leu Val Lys Ser Val Leu Asn Gly Asn Asp Asn Thr Ile Lys Glu Lys
        435                 440                 445
Arg Glu His Ile Asp Leu Asp Asp Phe Ser Lys Phe Gly Cys Asp Lys
    450                 455                 460
Asn Ser Val Asp Thr Asn Thr Lys Val Trp Glu Cys Lys Lys Pro Tyr
465                 470                 475                 480
Lys Leu Ser Thr Lys Asp Val Cys Val Pro Pro Arg Arg Gln Glu Leu
            485                 490                 495
Cys Leu Gly Asn Ile Asp Arg Ile Tyr Asp Lys Asn Leu Leu Met Ile
            500                 505                 510
Lys Glu His Ile Leu Ala Ile Ala Ile Tyr Glu Ser Arg Ile Leu Lys
        515                 520                 525
```

-continued

```
Arg Lys Tyr Lys Asn Lys Asp Asp Lys Glu Val Cys Lys Ile Ile Asn
        530                 535                 540
Lys Thr Phe Ala Asp Ile Arg Asp Ile Ile Gly Gly Thr Asp Tyr Trp
545                 550                 555                 560
Asn Asp Leu Ser Asn Arg Lys Leu Val Gly Lys Ile Asn Thr Asn Ser
                565                 570                 575
Asn Tyr Val His Arg Asn Lys Gln Asn Asp Lys Leu Phe Arg Asp Glu
            580                 585                 590
Trp Trp Lys Val Ile Lys Lys Asp Val Trp Asn Val Ile Ser Trp Val
        595                 600                 605
Phe Lys Asp Lys Thr Val Cys Lys Glu Asp Asp Ile Glu Asn Ile Pro
610                 615                 620
Gln Phe Phe Arg Trp Phe Ser Glu Trp Gly Asp Asp Tyr Cys Gln Asp
625                 630                 635                 640
Lys Thr Lys Met Ile Glu Thr Leu Lys Val Glu Cys Lys Glu Lys Pro
                645                 650                 655
Cys Glu Asp Asp Asn Cys Lys Arg Lys Cys Asn Ser Tyr Lys Glu Trp
            660                 665                 670
Ile Ser Lys Lys Lys Glu Glu Tyr Asn Lys Gln Ala Lys Gln Tyr Gln
        675                 680                 685
Glu Tyr Gln Lys Gly Asn Asn Tyr Lys Met Tyr Ser Glu Phe Lys Ser
690                 695                 700
Ile Lys Pro Glu Val Tyr Leu Lys Lys Tyr Ser Glu Lys Cys Ser Asn
705                 710                 715                 720
Leu Asn Phe Glu Asp Glu Phe Lys Glu Glu Leu His Ser Asp Tyr Lys
                725                 730                 735
Asn Lys Cys Thr Met Cys Pro Glu Val Lys Asp Val Pro Ile Ser Ile
            740                 745                 750
Ile Arg Asn Asn Glu Gln Thr Ser Gln Glu Ala Val Pro Glu Glu Ser
        755                 760                 765
Thr Glu Ile Ala His Arg Thr Glu Thr Arg Thr Asp Glu Arg Lys Asn
770                 775                 780
Gln Glu Pro Ala Asn Lys Asp Leu Lys Asn Pro Gln Gln Ser Val Gly
785                 790                 795                 800
Glu Asn Gly Thr Lys Asp Leu Leu Gln Glu Asp Leu Gly Gly Ser Arg
                805                 810                 815
Ser Glu Asp Glu Val Thr Gln Glu Phe Gly Val Asn His Gly Ile Pro
            820                 825                 830
Lys Gly Glu Asp Gln Thr Leu Gly Lys Ser Asp Ala Ile Pro Asn Ile
        835                 840                 845
Gly Glu Pro Glu Thr Gly Ile Ser Thr Glu Glu Ser Arg His Glu
850                 855                 860
Glu Gly His Asn Lys Gln Ala Leu Ser Thr Ser Val Asp Glu Pro Glu
865                 870                 875                 880
Leu Ser Asp Thr Leu Gln Leu His Glu Asp Thr Lys Glu Asn Asp Lys
                885                 890                 895
Leu Pro Leu Glu Ser Ser Thr Ile Thr Ser Pro Thr Glu Ser Gly Ser
            900                 905                 910
Ser Asp Thr Glu Glu Thr Pro Ser Ile Ser Glu Gly Pro Lys Gly Asn
        915                 920                 925
Glu Gln Lys Lys Arg Asp Asp Asp Ser Leu Ser Lys Ile Ser Val Ser
930                 935                 940
Pro Glu Asn Ser Arg Pro Glu Thr Asp Ala Lys Asp Thr Ser Asn Leu
```

-continued

```
            945                 950                 955                 960
Leu Lys Leu Lys Gly Asp Val Asp Ile Ser Met Pro Lys Ala Val Ile
                965                 970                 975
Gly Ser Ser Pro Asn Asp Asn Ile Asn Val Thr Glu Gln Gly Asp Asn
            980                 985                 990
Ile Ser Gly Val Asn Ser Lys Pro Leu Ser Asp Asp Val Arg Pro Asp
            995                 1000                1005
Lys Asn His Glu Glu Val Lys Glu His Thr Ser Asn Ser Asp Asn Val
        1010                1015                1020
Gln Gln Ser Gly Gly Ile Val Asn Met Asn Val Glu Lys Glu Leu Lys
1025                1030                1035                1040
Asp Thr Leu Glu Asn Pro Ser Ser Leu Asp Glu Gly Lys Ala His
            1045                1050                1055
Glu Glu Leu Ser Glu Pro Asn Leu Ser Ser Asp Gln Asp Met Ser Asn
        1060                1065                1070
Thr Pro Gly Pro Leu Asp Asn Thr Ser Glu Glu Thr Thr Glu Arg Ile
            1075                1080                1085
Ser Asn Asn Glu Tyr Lys Val Asn Glu Arg Glu Gly Glu Arg Thr Leu
        1090                1095                1100
Thr Lys Glu Tyr Glu Asp Ile Val Leu Lys Ser His Met Asn Arg Glu
1105                1110                1115                1120
Ser Asp Asp Gly Glu Leu Tyr Asp Glu Asn Ser Asp Leu Ser Thr Val
            1125                1130                1135
Asn Asp Glu Ser Glu Asp Ala Glu Ala Lys Met Lys Gly Asn Asp Thr
        1140                1145                1150
Ser Glu Met Ser His Asn Ser Ser Gln His Ile Glu Ser Asp Gln Gln
            1155                1160                1165
Lys Asn Asp Met Lys Thr Val Gly Asp Leu Gly Thr Thr His Val Gln
        1170                1175                1180
Asn Glu Ile Ser Val Pro Val Thr Gly Glu Ile Asp Glu Lys Leu Arg
1185                1190                1195                1200
Glu Ser Lys Glu Ser Lys Ile His Lys Ala Glu Glu Glu Arg Leu Ser
            1205                1210                1215
His Thr Asp Ile His Lys Ile Asn Pro Glu Asp Arg Asn Ser Asn Thr
            1220                1225                1230
Leu His Leu Lys Asp Ile Arg Asn Glu Glu Asn Glu Arg His Leu Thr
        1235                1240                1245
Asn Gln Asn Ile Asn Ile Ser Gln Glu Arg Asp Leu Gln Lys His Gly
        1250                1255                1260
Phe His Thr Met Asn Asn Leu His Gly Asp Gly Val Ser Glu Arg Ser
1265                1270                1275                1280
Gln Ile Asn His Ser His His Gly Asn Arg Gln Asp Arg Gly Gly Asn
            1285                1290                1295
Ser Gly Asn Val Leu Asn Met Arg Ser Asn Asn Asn Phe Asn Asn
            1300                1305                1310
Ile Pro Ser Arg Tyr Asn Leu Tyr Asp Lys Lys Leu Asp Leu Asp Leu
        1315                1320                1325
Tyr Glu Asn Arg Asn Asp Ser Thr Thr Lys Glu Leu Ile Lys Lys Leu
        1330                1335                1340
Ala Glu Ile Asn Lys Cys Glu Asn Glu Ile Ser Val Lys Tyr Cys Asp
1345                1350                1355                1360
His Met Ile His Glu Glu Ile Pro Leu Lys Thr Cys Thr Lys Glu Lys
            1365                1370                1375
```

```
Thr Arg Asn Leu Cys Cys Ala Val Ser Asp Tyr Cys Met Ser Tyr Phe
        1380            1385                1390

Thr Tyr Asp Ser Glu Glu Tyr Tyr Asn Cys Thr Lys Arg Glu Phe Asp
    1395                1400                1405

Asp Pro Ser Tyr Thr Cys Phe Arg Lys Glu Ala Phe Ser
    1410                1415                1420
```